United States Patent [19]
McGall et al.

[11] Patent Number: 6,156,501
[45] Date of Patent: *Dec. 5, 2000

[54] ARRAYS OF MODIFIED NUCLEIC ACID PROBES AND METHODS OF USE

[75] Inventors: Glenn Hugh McGall; Charles Garrett Miyada, both of Mountain View; Maureen T. Cronin, Los Altos; Jennifer Dee Tan, Newark; Mark S. Chee, Palo Alto, all of Calif.

[73] Assignee: Affymetrix, Inc., Santa Clara, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/630,427

[22] Filed: Apr. 3, 1996

Related U.S. Application Data

[63] Continuation-in-part of application No. 08/440,742, May 10, 1995, abandoned, which is a continuation-in-part of application No. PCT/US94/12305, Oct. 26, 1994, which is a continuation-in-part of application No. 08/284,064, Aug. 2, 1994, abandoned, which is a continuation-in-part of application No. 08/143,312, Oct. 26, 1993, abandoned.

[51] Int. Cl.[7] .............................. C12Q 1/68; C07H 21/00
[52] U.S. Cl. ................... 435/6; 422/50; 422/68.1; 435/283.1; 435/287.1; 435/287.2; 435/288.3; 435/288.7; 435/289.1; 435/299.1; 435/305.1; 436/501; 536/22.1; 536/24.1; 536/24.3; 536/24.31; 536/24.32; 536/24.33
[58] Field of Search ................... 422/50, 68.1; 435/6, 435/810, 283.1, 287.1, 287.2, 288.3, 288.7, 289.1, 299.1, 305.1; 436/501; 536/23.1, 24.1, 22.1, 24.3–24.33; 935/77, 78

[56] References Cited

U.S. PATENT DOCUMENTS

| | | | |
|---|---|---|---|
| 5,002,867 | 3/1991 | Macevicz | 435/6 |
| 5,143,854 | 9/1992 | Pirrung et al. | 436/518 |
| 5,200,051 | 4/1993 | Cozzette et al. | 204/403 |
| 5,202,231 | 4/1993 | Drmanac et al. | 435/6 |
| 5,217,866 | 6/1993 | Summerton et al. | 435/6 |
| 5,412,087 | 5/1995 | McGall et al. | 536/24.3 |
| 5,474,796 | 12/1995 | Brennan | 427/2.13 |
| 5,484,908 | 1/1996 | Froehler et al. | 536/24.31 |
| 5,527,681 | 6/1996 | Holmes | 435/6 |
| 5,556,752 | 9/1996 | Lockhart et al. | 435/6 |
| 5,556,961 | 9/1996 | Foote et al. | 536/27.1 |
| 5,604,097 | 2/1997 | Brenner | 435/6 |
| 5,800,992 | 9/1998 | Fodor et al. | 435/6 |
| 5,821,060 | 10/1998 | Arlinghaus et al. | 435/6 |
| B1 4,683,202 | 11/1990 | Mullis | 435/91 |

FOREIGN PATENT DOCUMENTS

| | | | |
|---|---|---|---|
| 8605518 | 9/1986 | WIPO | |
| WO 89/10977 | 11/1989 | WIPO | |
| WO 89/11548 | 11/1989 | WIPO | |
| WO90/04652 | 5/1990 | WIPO | C12Q 1/68 |
| WO 92/10092 | 6/1992 | WIPO | |
| WO 93/17126 | 9/1993 | WIPO | |

OTHER PUBLICATIONS

Durland, Ross H., et al. (1995) "Selective Binding of Pyrido[2, 3–d]pyrimidine 2'–Deoxyribonucleoside to AT Base Pairs in Antiparallel Triple Helices", *Bioconjugate Chem* 6:278–282.

*Primary Examiner*—Ardin H. Marschel
*Attorney, Agent, or Firm*—Townsend and Townsend and Crew

[57] ABSTRACT

Oligonucleotide analogue arrays attached to solid substrates and methods related to the use thereof are provided. The oligonucleotide analogues hybridize to nucleic acids with either higher or lower specificity than corresponding unmodified oligonucleotides. Target nucleic acids which comprise nucleotide analogues are bound to oligonucleotide and oligonucleotide analogue arrays.

72 Claims, 5 Drawing Sheets

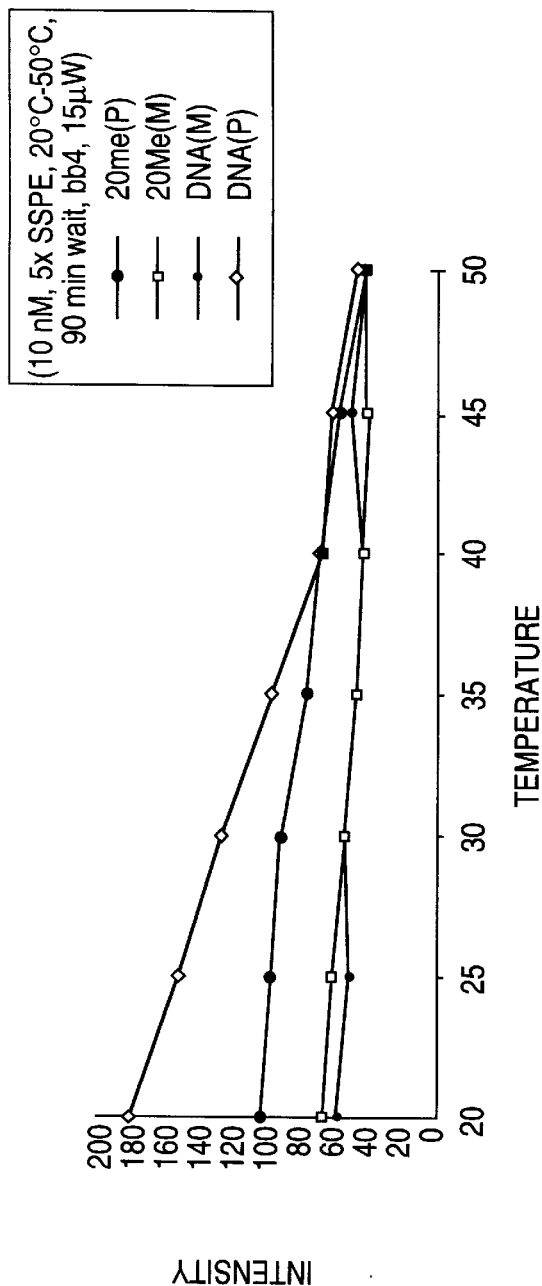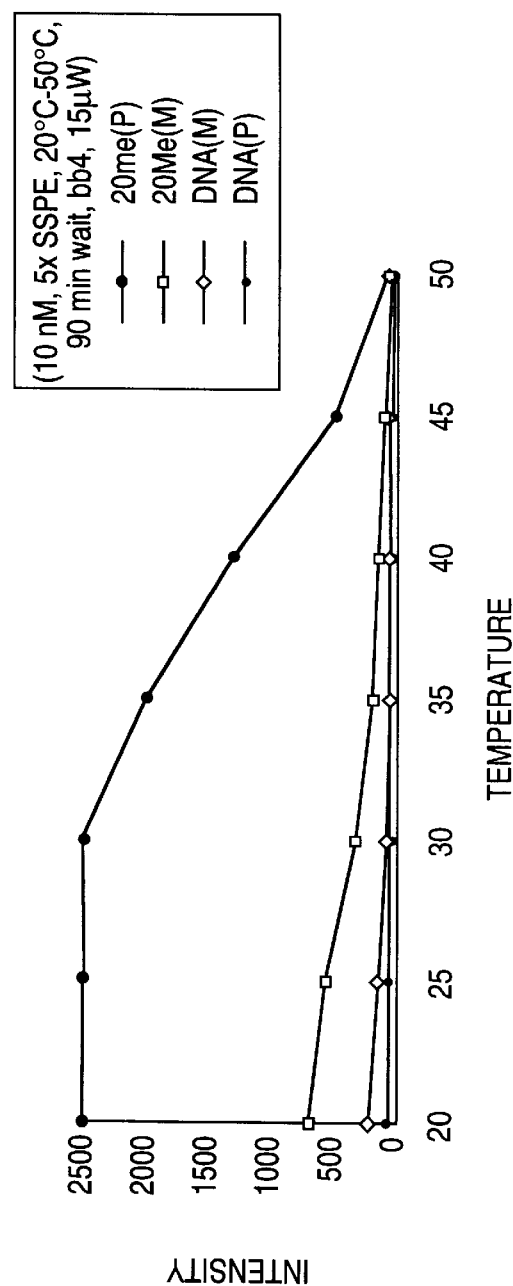

SEQUENCE LISTING (1) GENERAL INFORMATION:

(iii) NUMBER OF SEQUENCES: 29

(2) INFORMATION FOR SEQ ID NO:1:

(i) SEQUENCE CHARACTERISTICS:
      (A) LENGTH: 10 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:1:

AAGATGCTAC                                                                        10

(2) INFORMATION FOR SEQ ID NO:2:

(i) SEQUENCE CHARACTERISTICS:
      (A) LENGTH: 11 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:2:

AAAAANAAAA A                                                                   11

(2) INFORMATION FOR SEQ ID NO:3:

(i) SEQUENCE CHARACTERISTICS:
      (A) LENGTH: 10 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:3:

ATATAATATA                                                                     10

(2) INFORMATION FOR SEQ ID NO:4:

(i) SEQUENCE CHARACTERISTICS:
      (A) LENGTH: 10 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:4:

CGCGCCGCGC                                                                              10

(2) INFORMATION FOR SEQ ID NO:5:

(i) SEQUENCE CHARACTERISTICS:
             (A) LENGTH: 15 base pairs
             (B) TYPE: nucleic acid
             (C) STRANDEDNESS: single
             (D) TOPOLOGY: linear (ii) MOLECULE TYPE: DNA (ix) FEATURE:
             (A) NAME/KEY: modified_base
             (B) LOCATION: 6..10
             (D) OTHER INFORMATION: /mod_base= OTHER
                   /note= "N = guanosine (G),
                   2',3'-dideoxyguanine (ddG),
                   2'-deoxyinosine (dI) or thymine (T)"

(xi) SEQUENCE DESCRIPTION: SEQ ID NO:5:

TGGGCNNNNN TTGTA                                                                        15

(2) INFORMATION FOR SEQ ID NO:6:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: DNA (ix) FEATURE:
             (A) NAME/KEY: -
             (B) LOCATION: 1..20
             (D) OTHER INFORMATION: /note= "Target DNA sequence"

(xi) SEQUENCE DESCRIPTION: SEQ ID NO:6:

CTGAACGGTA GCATCTTGAC                                                                   20

(2) INFORMATION FOR SEQ ID NO:7:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: DNA (ix) FEATURE:
             (A) NAME/KEY: -
             (B) LOCATION: 1..20
             (D) OTHER INFORMATION: /note= "Complementary DNA sequence"

(xi) SEQUENCE DESCRIPTION: SEQ ID NO:7:

GTCAAGATGC TACCGTTCAG                                                                   20

(2) INFORMATION FOR SEQ ID NO:8:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: RNA (ix) FEATURE:
            (A) NAME/KEY: -
            (B) LOCATION: 1..20
            (D) OTHER INFORMATION: /note= "Target RNA sequence"

(xi) SEQUENCE DESCRIPTION: SEQ ID NO:8:

CUGAACGGUA GCAUCUUGAC                                                        20

(2) INFORMATION FOR SEQ ID NO:9:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "2'-O-methyl oligonucleotide"

(ix) FEATURE:
            (A) NAME/KEY: modified_base
            (B) LOCATION: 1
            (D) OTHER INFORMATION: /mod_base= cm (ix) FEATURE:
            (A) NAME/KEY: modified_base
            (B) LOCATION: 2
            (D) OTHER INFORMATION: /mod_base= um (ix) FEATURE:
            (A) NAME/KEY: modified_base
            (B) LOCATION: 3
            (D) OTHER INFORMATION: /mod_base= gm (ix) FEATURE:
            (A) NAME/KEY: modified_base
            (B) LOCATION: 4
            (D) OTHER INFORMATION: /mod_base= OTHER
                /note= "2'-O-methyladenosine"

(ix) FEATURE:
            (A) NAME/KEY: modified_base
            (B) LOCATION: 5
            (D) OTHER INFORMATION: /mod_base= OTHER
                /note= "2'-O-methyladenosine"

(ix) FEATURE:
            (A) NAME/KEY: modified_base
            (B) LOCATION: 6
            (D) OTHER INFORMATION: /mod_base= cm (ix) FEATURE:
            (A) NAME/KEY: modified_base
            (B) LOCATION: 7
            (D) OTHER INFORMATION: /mod_base= gm (ix) FEATURE:
            (A) NAME/KEY: modified_base
            (B) LOCATION: 8
            (D) OTHER INFORMATION: /mod_base= gm (ix) FEATURE:
            (A) NAME/KEY: modified_base
            (B) LOCATION: 9
            (D) OTHER INFORMATION: /mod_base= um (ix) FEATURE:
            (A) NAME/KEY: modified_base
            (B) LOCATION: 10
            (D) OTHER INFORMATION: /mod_base= OTHER
                /note= "2'-O-methyladenosine"

```
    (ix) FEATURE:
         (A) NAME/KEY: modified_base
         (B) LOCATION: 11
         (D) OTHER INFORMATION: /mod_base= gm (ix) FEATURE:
         (A) NAME/KEY: modified_base
         (B) LOCATION: 12
         (D) OTHER INFORMATION: /mod_base= cm (ix) FEATURE:
         (A) NAME/KEY: modified_base
         (B) LOCATION: 13
         (D) OTHER INFORMATION: /mod_base= OTHER
             /note= "2'-O-methyladenosine"

(ix) FEATURE:
         (A) NAME/KEY: modified_base
         (B) LOCATION: 14
         (D) OTHER INFORMATION: /mod_base= um (ix) FEATURE:
         (A) NAME/KEY: modified_base
         (B) LOCATION: 15
         (D) OTHER INFORMATION: /mod_base= cm (ix) FEATURE:
         (A) NAME/KEY: modified_base
         (B) LOCATION: 16
         (D) OTHER INFORMATION: /mod_base= um (ix) FEATURE:
         (A) NAME/KEY: modified_base
         (B) LOCATION: 17
         (D) OTHER INFORMATION: /mod_base= um (ix) FEATURE:
         (A) NAME/KEY: modified_base
         (B) LOCATION: 18
         (D) OTHER INFORMATION: /mod_base= gm (ix) FEATURE:
         (A) NAME/KEY: modified_base
         (B) LOCATION: 19
         (D) OTHER INFORMATION: /mod_base= OTHER
             /note= "2'-O-methyladenosine"

(ix) FEATURE:
         (A) NAME/KEY: modified_base
         (B) LOCATION: 20
         (D) OTHER INFORMATION: /mod_base= cm (ix) FEATURE:
         (A) NAME/KEY: -
         (B) LOCATION: 1..20
         (D) OTHER INFORMATION: /note= "Target 2'-O-methyl
             oligonucleotide sequence"

(xi) SEQUENCE DESCRIPTION: SEQ ID NO:9:

NNNNNNNNNN NNNNNNNNNN                                                       20

(2) INFORMATION FOR SEQ ID NO:10:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (ii) MOLECULE TYPE: DNA (ix) FEATURE:
         (A) NAME/KEY: -
         (B) LOCATION: 1..8
         (D) OTHER INFORMATION: /note= "Matching DNA oligonucleotide
             probe"
```

-continued

```
    (xi) SEQUENCE DESCRIPTION: SEQ ID NO:10:

CTTGCCAT                                                                      8

(2) INFORMATION FOR SEQ ID NO:11:

(i) SEQUENCE CHARACTERISTICS:
         (A) LENGTH: 8 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "2'-O-methyl oligonucleotide"

(ix) FEATURE:
         (A) NAME/KEY: modified_base
         (B) LOCATION: 1
         (D) OTHER INFORMATION: /mod_base= cm (ix) FEATURE:
         (A) NAME/KEY: modified_base
         (B) LOCATION: 2
         (D) OTHER INFORMATION: /mod_base= um (ix) FEATURE:
         (A) NAME/KEY: modified_base
         (B) LOCATION: 3
         (D) OTHER INFORMATION: /mod_base= um (ix) FEATURE:
         (A) NAME/KEY: modified_base
         (B) LOCATION: 4
         (D) OTHER INFORMATION: /mod_base= gm (ix) FEATURE:
         (A) NAME/KEY: modified_base
         (B) LOCATION: 5
         (D) OTHER INFORMATION: /mod_base= cm (ix) FEATURE:
         (A) NAME/KEY: modified_base
         (B) LOCATION: 6
         (D) OTHER INFORMATION: /mod_base= cm (ix) FEATURE:
         (A) NAME/KEY: modified_base
         (B) LOCATION: 7
         (D) OTHER INFORMATION: /mod_base= OTHER
             /note= "2'-O-methyladenosine"

(ix) FEATURE:
         (A) NAME/KEY: modified_base
         (B) LOCATION: 8
         (D) OTHER INFORMATION: /mod_base= um (ix) FEATURE:
         (A) NAME/KEY: -
         (B) LOCATION: 1..8
         (D) OTHER INFORMATION: /note= "Matching 2'-O-methyl
             oligonucleotide analogue probe"

(xi) SEQUENCE DESCRIPTION: SEQ ID NO:11:

NNNNNNNN                                                                      8

(2) INFORMATION FOR SEQ ID NO:12:

(i) SEQUENCE CHARACTERISTICS:
         (A) LENGTH: 8 base pairs
         (B) TYPE: nucleic acid
         (C) STRANDEDNESS: single
         (D) TOPOLOGY: linear (ii) MOLECULE TYPE: DNA (ix) FEATURE:
```

-continued

```
            (A) NAME/KEY: -
            (B) LOCATION: 1..8
            (D) OTHER INFORMATION: /note= "DNA oligonucleotide probe
                  with 1 base mismatch"

(xi) SEQUENCE DESCRIPTION: SEQ ID NO:12:

CTTGCTAT                                                                   8

(2) INFORMATION FOR SEQ ID NO:13:

(i) SEQUENCE CHARACTERISTICS:
            (A) LENGTH: 8 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "2'-O-methyl oligonucleotide"

(ix) FEATURE:
            (A) NAME/KEY: modified_base
            (B) LOCATION: 1
            (D) OTHER INFORMATION: /mod_base= cm (ix) FEATURE:
            (A) NAME/KEY: modified_base
            (B) LOCATION: 2
            (D) OTHER INFORMATION: /mod_base= um (ix) FEATURE:
            (A) NAME/KEY: modified_base
            (B) LOCATION: 3
            (D) OTHER INFORMATION: /mod_base= um (ix) FEATURE:
            (A) NAME/KEY: modified_base
            (B) LOCATION: 4
            (D) OTHER INFORMATION: /mod_base= gm (ix) FEATURE:
            (A) NAME/KEY: modified_base
            (B) LOCATION: 5
            (D) OTHER INFORMATION: /mod_base= cm (ix) FEATURE:
            (A) NAME/KEY: modified_base
            (B) LOCATION: 6
            (D) OTHER INFORMATION: /mod_base= um (ix) FEATURE:
            (A) NAME/KEY: modified_base
            (B) LOCATION: 7
            (D) OTHER INFORMATION: /mod_base= OTHER
                  /note= "2'-O-methyladenosine"

(ix) FEATURE:
            (A) NAME/KEY: modified_base
            (B) LOCATION: 8
            (D) OTHER INFORMATION: /mod_base= um (ix) FEATURE:
            (A) NAME/KEY: -
            (B) LOCATION: 1..8
            (D) OTHER INFORMATION: /note= "2'-O-methyl oligonucleotide
                  analogue probe with 1 base mismatch"

(xi) SEQUENCE DESCRIPTION: SEQ ID NO:13:

NNNNNNNN                                                                   8

(2) INFORMATION FOR SEQ ID NO:14:

(i) SEQUENCE CHARACTERISTICS:
            (A) LENGTH: 10 base pairs
            (B) TYPE: nucleic acid
```

```
        (C) STRANDEDNESS: single
        (D) TOPOLOGY: linear (ii) MOLECULE TYPE: DNA (ix) FEATURE:
        (A) NAME/KEY: modified_base
        (B) LOCATION: 10
        (D) OTHER INFORMATION: /mod_base= OTHER
            /note= "N = cytosine covalently
            modified at the 3' phosphate group with
            a hexaethyleneglycol (HEG) linker"

(xi) SEQUENCE DESCRIPTION: SEQ ID NO:14:

AAGATGNTAN                                                                     10

(2) INFORMATION FOR SEQ ID NO:15:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 10
        (D) OTHER INFORMATION: /mod_base= OTHER
            /note= "N = cytosine covalently modified
            at the 3' phosphate group with a
            hexaethyleneglycol (HEG) linker"

(xi) SEQUENCE DESCRIPTION: SEQ ID NO:15:

AAGATNCTAN                                                                     10

(2) INFORMATION FOR SEQ ID NO:16:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 10
        (D) OTHER INFORMATION: /mod_base= OTHER
            /note= "N = cytosine covalently modified
            at the 3' phosphate group with a
            hexaethyleneglycol (HEG) linker"

(xi) SEQUENCE DESCRIPTION: SEQ ID NO:16:

AAGANGCTAN                                                                     10

(2) INFORMATION FOR SEQ ID NO:17:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 10
        (D) OTHER INFORMATION: /mod_base= OTHER
            /note= "N = cytosine covalently modified
```

```
            at the 3' phosphate group with a
            hexaethyleneglycol (HEG) linker"

(xi) SEQUENCE DESCRIPTION: SEQ ID NO:17:

AAGNTGCTAN                                                              10

(2) INFORMATION FOR SEQ ID NO:18:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 1
        (D) OTHER INFORMATION: /mod_base= OTHER
            /note= "N = cytosine covalently modified
            at the 5' phosphate group with a
            fluorescein molecule"

(xi) SEQUENCE DESCRIPTION: SEQ ID NO:18:

NTGAACGGTA GCATCTTGAC                                                   20

(2) INFORMATION FOR SEQ ID NO:19:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 11
        (D) OTHER INFORMATION: /mod_base= OTHER
            /note= "N = adenine covalently modified
            at the 3' phosphate group with a
            hexaethyleneglycol (HEG) linker"

(xi) SEQUENCE DESCRIPTION: SEQ ID NO:19:

AAAAANAAAA N                                                            11

(2) INFORMATION FOR SEQ ID NO:20:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 1
        (D) OTHER INFORMATION: /mod_base= OTHER
            /note= "N = thymine covalently modified
            at the 5' phosphate group with a
            fluorescein molecule"

(xi) SEQUENCE DESCRIPTION: SEQ ID NO:20:

NTTTTGTTTT T                                                            11
```

(2) INFORMATION FOR SEQ ID NO:21:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 10
        (D) OTHER INFORMATION: /mod_base= OTHER
           /note= "N = cytosine covalently modified
           at the 3' phosphate group with a
           hexaethyleneglycol (HEG) linker"

(xi) SEQUENCE DESCRIPTION: SEQ ID NO:21:

CGCGCCGCGN           10

(2) INFORMATION FOR SEQ ID NO:22:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "2'-deoxynucleoside/nucleoside
           analogue decanucleotide probe"

(ix) FEATURE:
        (A) NAME/KEY: modified_base
        (B) LOCATION: 1
        (D) OTHER INFORMATION: /mod_base= OTHER
           /note= "N = 2'-deoxyadenosine"

(ix) FEATURE:
        (A) NAME/KEY: modified_base
        (B) LOCATION: 3
        (D) OTHER INFORMATION: /mod_base= OTHER
           /note= "N = 2'-deoxyadenosine"

(ix) FEATURE:
        (A) NAME/KEY: modified_base
        (B) LOCATION: 5
        (D) OTHER INFORMATION: /mod_base= OTHER
           /note= "N = 2'-deoxyadenosine"

(ix) FEATURE:
        (A) NAME/KEY: modified_base
        (B) LOCATION: 6
        (D) OTHER INFORMATION: /mod_base= OTHER
           /note= "N = 2'-deoxyadenosine"

(ix) FEATURE:
        (A) NAME/KEY: modified_base
        (B) LOCATION: 8
        (D) OTHER INFORMATION: /mod_base= OTHER
           /note= "N = 2'-deoxyadenosine"

(ix) FEATURE:
        (A) NAME/KEY: modified_base
        (B) LOCATION: 10
        (D) OTHER INFORMATION: /mod_base= OTHER
           /note= "N = 2'-deoxyadenosine covalently
           modified at the 3' phosphate group with
           a hexaethyleneglycol (HEG) linker"

(xi) SEQUENCE DESCRIPTION: SEQ ID NO:22:

NTNTNNTNTN           10

```
(2) INFORMATION FOR SEQ ID NO:23:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "2'-deoxynucleoside/nucleoside
            analogue decanucleotide probe"

(ix) FEATURE:
        (A) NAME/KEY: modified_base
        (B) LOCATION: 1
        (D) OTHER INFORMATION: /mod_base= OTHER
            /note= "N = 2'-deoxyadenosine"

(ix) FEATURE:
        (A) NAME/KEY: modified_base
        (B) LOCATION: 2
        (D) OTHER INFORMATION: /mod_base= OTHER
            /note= "N = 5-propynyl-2'-deoxyuridine"

(ix) FEATURE:
        (A) NAME/KEY: modified_base
        (B) LOCATION: 3
        (D) OTHER INFORMATION: /mod_base= OTHER
            /note= "N = 2'-deoxyadenosine"

(ix) FEATURE:
        (A) NAME/KEY: modified_base
        (B) LOCATION: 4
        (D) OTHER INFORMATION: /mod_base= OTHER
            /note= "N = 5-propynyl-2'-deoxyuridine"

(ix) FEATURE:
        (A) NAME/KEY: modified_base
        (B) LOCATION: 5
        (D) OTHER INFORMATION: /mod_base= OTHER
            /note= "N = 2'-deoxyadenosine"

(ix) FEATURE:
        (A) NAME/KEY: modified_base
        (B) LOCATION: 6
        (D) OTHER INFORMATION: /mod_base= OTHER
            /note= "N = 2'-deoxyadenosine"

(ix) FEATURE:
        (A) NAME/KEY: modified_base
        (B) LOCATION: 7
        (D) OTHER INFORMATION: /mod_base= OTHER
            /note= "N = 5-propynyl-2'-deoxyuridine"

(ix) FEATURE:
        (A) NAME/KEY: modified_base
        (B) LOCATION: 8
        (D) OTHER INFORMATION: /mod_base= OTHER
            /note= "N = 2'-deoxyadenosine"

(ix) FEATURE:
        (A) NAME/KEY: modified_base
        (B) LOCATION: 9
        (D) OTHER INFORMATION: /mod_base= OTHER
            /note= "N = 5-propynyl-2'-deoxyuridine"

(ix) FEATURE:
        (A) NAME/KEY: modified_base
        (B) LOCATION: 10
        (D) OTHER INFORMATION: /mod_base= OTHER
            /note= "N = 2'-deoxyadenosine covalently
            modified at the 3' phosphate group with
            a hexaethyleneglycol (HEG) linker"

(xi) SEQUENCE DESCRIPTION: SEQ ID NO:23:

NNNNNNNNNN                                                              10
```

(2) INFORMATION FOR SEQ ID NO:24:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "2'-deoxynucleoside/nucleoside
            analogue decanucleotide probe"

(ix) FEATURE:
        (A) NAME/KEY: modified_base
        (B) LOCATION: 1
        (D) OTHER INFORMATION: /mod_base= OTHER
            /note= "N = 2-amino-2'-deoxyadenosine"

(ix) FEATURE:
        (A) NAME/KEY: modified_base
        (B) LOCATION: 3
        (D) OTHER INFORMATION: /mod_base= OTHER
            /note= "N = 2-amino-2'-deoxyadenosine"

(ix) FEATURE:
        (A) NAME/KEY: modified_base
        (B) LOCATION: 5
        (D) OTHER INFORMATION: /mod_base= OTHER
            /note= "N = 2-amino-2'-deoxyadenosine"

(ix) FEATURE:
        (A) NAME/KEY: modified_base
        (B) LOCATION: 6
        (D) OTHER INFORMATION: /mod_base= OTHER
            /note= "N = 2-amino-2'-deoxyadenosine"

(ix) FEATURE:
        (A) NAME/KEY: modified_base
        (B) LOCATION: 8
        (D) OTHER INFORMATION: /mod_base= OTHER
            /note= "N = 2-amino-2'-deoxyadenosine"

(ix) FEATURE:
        (A) NAME/KEY: modified_base
        (B) LOCATION: 10
        (D) OTHER INFORMATION: /mod_base= OTHER
            /note= "N = 2-amino-2'-deoxyadenosine
            covalently modified at the 3'
            phosphate group with a
            hexaethyleneglycol (HEG) linker"

(xi) SEQUENCE DESCRIPTION: SEQ ID NO:24:

NTNTNNTNTN                                                                10

(2) INFORMATION FOR SEQ ID NO:25:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "2'-deoxynucleoside/nucleoside
            analogue decanucleotide probe"

(ix) FEATURE:
        (A) NAME/KEY: modified_base
        (B) LOCATION: 1
        (D) OTHER INFORMATION: /mod_base= OTHER
            /note= "N = 2-amino-2'-deoxyadenosine"

(ix) FEATURE:
        (A) NAME/KEY: modified_base
        (B) LOCATION: 2
        (D) OTHER INFORMATION: /mod_base= OTHER
            /note= "N = 5-propynyl-2'-deoxyuridine"

```
        (ix) FEATURE:
              (A) NAME/KEY: modified_base
              (B) LOCATION: 3
              (D) OTHER INFORMATION: /mod_base= OTHER
                  /note= "N = 2-amino-2'-deoxyadenosine"

(ix) FEATURE:
              (A) NAME/KEY: modified_base
              (B) LOCATION: 4
              (D) OTHER INFORMATION: /mod_base= OTHER
                  /note= "N = 5-propynyl-2'-deoxyuridine"

(ix) FEATURE:
              (A) NAME/KEY: modified_base
              (B) LOCATION: 5
              (D) OTHER INFORMATION: /mod_base= OTHER
                  /note= "N = 2-amino-2'-deoxyadenosine"

(ix) FEATURE:
              (A) NAME/KEY: modified_base
              (B) LOCATION: 6
              (D) OTHER INFORMATION: /mod_base= OTHER
                  /note= "N = 2-amino-2'-deoxyadenosine"

(ix) FEATURE:
              (A) NAME/KEY: modified_base
              (B) LOCATION: 7
              (D) OTHER INFORMATION: /mod_base= OTHER
                  /note= "N = 5-propynyl-2'-deoxyuridine"

(ix) FEATURE:
              (A) NAME/KEY: modified_base
              (B) LOCATION: 8
              (D) OTHER INFORMATION: /mod_base= OTHER
                  /note= "N = 2-amino-2'-deoxyadenosine"

(ix) FEATURE:
              (A) NAME/KEY: modified_base
              (B) LOCATION: 9
              (D) OTHER INFORMATION: /mod_base= OTHER
                  /note= "N = 5-propynyl-2'-deoxyuridine"

(ix) FEATURE:
              (A) NAME/KEY: modified_base
              (B) LOCATION: 10
              (D) OTHER INFORMATION: /mod_base= OTHER
                  /note= "N = 2-amino-2'-deoxyadenosine
                  covalently modified at the 3'
                  phosphate group with a
                  hexaethyleneglycol (HEG) linker"

(xi) SEQUENCE DESCRIPTION: SEQ ID NO:25:

NNNNNNNNNN                                                                    10

(2) INFORMATION FOR SEQ ID NO:26:

(i) SEQUENCE CHARACTERISTICS:
              (A) LENGTH: 10 base pairs
              (B) TYPE: nucleic acid
              (C) STRANDEDNESS: single
              (D) TOPOLOGY: linear (ii) MOLECULE TYPE: DNA (ix) FEATURE:
              (A) NAME/KEY: modified_base
              (B) LOCATION: 1
              (D) OTHER INFORMATION: /mod_base= OTHER
                  /note= "N = thymine covalently modified
                  at the 5' hydroxyl group with a
                  fluorescein molecule"

(ix) FEATURE:
              (A) NAME/KEY: modified_base
              (B) LOCATION: 10
              (D) OTHER INFORMATION: /mod_base= OTHER
```

-continued

```
              /note= "N = thymine covalently modified
              at the 3' phosphate group with a
              hexaethyleneglycol (HEG) linker which is
              covalently bound to the 5' phosphate
              group of the 5' guanine (N in pos. 1) of
              SEQ ID NO:27"

(xi) SEQUENCE DESCRIPTION: SEQ ID NO:26:

NATATTATAN                                                              10

(2) INFORMATION FOR SEQ ID NO:27:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 1
        (D) OTHER INFORMATION: /mod_base= OTHER
              /note= "N = guanine covalently modified
              at the 5' phosphate group with a
              hexaethyleneglycol (HEG) linker which is
              covalently bound to the 3' phosphate
              group of the 3' thymine (N in pos. 10)
              of SEQ ID NO:26"

(xi) SEQUENCE DESCRIPTION: SEQ ID NO:27:

NCGCGGCGCG                                                              10

(2) INFORMATION FOR SEQ ID NO:28:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 6..10
        (D) OTHER INFORMATION: /mod_base= OTHER
              /note= "N = guanine (G),
              2',3'-dideoxyguanine (ddG),
              2'-deoxyinosine (dI) or thymine (T)"

(ix) FEATURE:
        (A) NAME/KEY: modified_base
        (B) LOCATION: 15
        (D) OTHER INFORMATION: /mod_base= OTHER
              /note= "N = cytosine covalently modified
              at the 5' phosphate group with a
              hexaethyleneglycol (HEG) linker"

(xi) SEQUENCE DESCRIPTION: SEQ ID NO:28:

TGGGCNNNNN TTGTN                                                        15

(2) INFORMATION FOR SEQ ID NO:29:

(i) SEQUENCE CHARACTERISTICS:
        (A) LENGTH: 21 base pairs
        (B) TYPE: nucleic acid
        (C) STRANDEDNESS: single
        (D) TOPOLOGY: linear
```

```
ks(ii)  MOLECULE  TYPE:  DNA
   (ix) FEATURE:
        (A) NAME/KEY: modified_base
        (B) LOCATION: 1
        (D) OTHER INFORMATION: /mod_base= OTHER
            /note= "N = cytosine covalently modified
            at the 5' phosphate group with a
            fluorescein molecule"

(xi) SEQUENCE DESCRIPTION: SEQ ID NO:29:

NAATACAACC CCCGCCCATC C                                              21
```

ARRAYS OF MODIFIED NUCLEIC ACID PROBES AND METHODS OF USE

CROSS-REFERENCE TO RELATED APPLICATION

This application is a continuation-in-part of U.S. Ser. No. 08/440,742 filed May 10, 1995 abandoned, which is a continuation-in-part of PCT application (designating the United States) SN PCT/US94/12305 filed Oct. 26, 1994, which is a continuation-in-part of U.S. Ser. No. 08/284,064 filed Aug. 2, 1994 abandoned, which is a continuation-in-part of U.S. Ser. No 08/143,312 filed Oct. 26, 1993 abandoned, each of which is incorporated herein by reference in its entirety for all purposes.

FIELD OF THE INVENTION

The present invention provides probes comprised of nucleotide analogues immobilized in arrays on solid substrates for analyzing molecular interactions of biological interest, and target nucleic acids comprised of nucleotide analogues. The invention therefore relates to the molecular interaction of polymers immobilized on solid substrates including related chemistry, biology, and medical diagnostic uses.

BACKGROUND OF THE INVENTION

The development of very large scale immobilized polymer synthesis (VLSIPS™) technology provides pioneering methods for arranging large numbers of oligonucleotide probes in very small arrays. See, U.S. application Ser. No. 07/805,727 now U.S. Pat. No. 5,424,186 and PCT patent publication Nos. WO 90/15070 and 92/10092, each of which is incorporated herein by reference for all purposes. U.S. patent application Ser. No. 08/082,937, filed Jun. 25, 1993, and incorporated herein for all purposes, describes methods for making arrays of oligonucleotide probes that are used, e.g., to determine the complete sequence of a target nucleic acid and/or to detect the presence of a nucleic acid with a specified sequence.

VLSIPS™ technology provides an efficient means for large scale production of miniaturized oligonucleotide arrays for sequencing by hybridization (SBH), diagnostic testing for inherited or somatically acquired genetic diseases, and forensic analysis. Other applications include determination of sequence specificity of nucleic acids, protein-nucleic acid complexes and other polymer-polymer interactions.

SUMMARY OF THE INVENTION

The present invention provides arrays of oligonucleotide analogues attached to solid substrates. Oligonucleotide analogues have different hybridization properties than oligonucleotides based upon naturally occurring nucleotides. By incorporating oligonucleotide analogues into the arrays of the invention, hybridization to a target nucleic acid is optimized.

The oligonucleotide analogue arrays have virtually any number of different members, determined largely by the number or variety of compounds to be screened against the array in a given application. In one group of embodiments, the array has from 10 up to 100 oligonucleotide analogue members. In other groups of embodiments, the arrays have between 100 and 10,000 members, and in yet other embodiments the arrays have between 10,000 and 1,000,0000 members. In preferred embodiments, the array will have a density of more than 100 members at known locations per $cm^2$, or more preferably, more than 1000 members per $cm^2$. In some embodiments, the arrays have a density of more than 10,000 members per $cm^2$.

The solid substrate upon which the array is constructed includes any material upon which oligonucleotide analogues are attached in a defined relationship to one another, such as beads, arrays, and slides. Especially preferred oligonucleotide analogues of the array are between about 5 and about 20 nucleotides, nucleotide analogues or a mixture thereof in length.

In one group of embodiments, nucleoside analogues incorporated into the oligonucleotide analogues of the array will have the chemical formula:

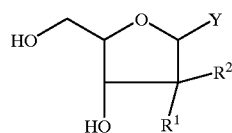

wherein $R^1$ and $R^2$ are independently selected from the group consisting of hydrogen, methyl, hydroxy, alkoxy (e.g., methoxy, ethoxy, propoxy, allyloxy, and propargyloxy), alkylthio, halogen (Fluorine, Chlorine, and Bromine), cyano, and azido, and wherein Y is a heterocyclic moiety, e.g., a base selected from the group consisting of purines, purine analogues, pyrimidines, pyrimidine analogues, universal bases (e.g., 5-nitroindole) or other groups or ring systems capable of forming one or more hydrogen bonds with corresponding moieties on alternate strands within a double- or triple-stranded nucleic acid or nucleic acid analogue, or other groups or ring systems capable of forming nearest-neighbor base-stacking interactions within a double- or triple-stranded complex. In other embodiments, the oligonucleotide analogues are not constructed from nucleosides, but are capable of binding to nucleic acids in solution due to structural similarities between the oligonucleotide analogue and a naturally occurring nucleic acid. An example of such an oligonucleotide analogue is a peptide nucleic acid or polyamide nucleic acid in which bases which hydrogen bond to a nucleic acid are attached to a polyamide backbone.

The present invention also provides target nucleic acids hybridized to oligonucleotide arrays. In the target nucleic acids of the invention, nucleotide analogues are incorporated into the target nucleic acid, altering the hybridization properties of the target nucleic acid to an array of oligonucleotide probes. Typically, the oligonucleotide probe arrays also comprise nucleotide analogues.

The target nucleic acids are typically synthesized by providing a nucleotide analogue as a reagent during the enzymatic copying of a nucleic acid. For instance, nucleotide analogues are incorporated into polynucleic acid analogues using taq polymerase in a PCR reaction. Thus, a nucleic acid containing a sequence to be analyzed is typically amplified in a PCR or RNA amplification procedure with nucleotide analogues, and the resulting target nucleic acid analogue amplicon is hybridized to a nucleic acid analogue array.

Oligonucleotide analogue arrays and target nucleic acids are optionally composed of oligonucleotide analogues which are resistant to hydrolysis or degradation by nuclease enzymes such as RNAase A. This has the advantage of providing the array or target nucleic acid with greater longevity by rendering it resistant to enzymatic degradation.

For example, analogues comprising 2'-O-methyloligoribonucleotides are resistant to RNAase A.

Oligonucleotide analogue arrays are optionally arranged into libraries for screening compounds for desired characteristics, such as the ability to bind a specified oligonucleotide analogue, or oligonucleotide analogue-containing structure. The libraries also include oligonucleotide analogue members which form conformationally-restricted probes, such as unimolecular double-stranded probes or unimolecular double-stranded probes which present a third chemical structure of interest. For instance, the array of oligonucleotide analogues optionally include a plurality of different members, each member having the formula: $Y—L^1—X^1—L^2—X^2$, wherein Y is a solid substrate, $X^1$ and $X^2$ are complementary oligonucleotides containing at least one nucleotide analogue, $L^1$ is a spacer, and $L^2$ is a linking group having sufficient length such that $X^1$ and $X^2$ form a double-stranded oligonucleotide. An array of such members comprise a library of unimolecular double-stranded oligonucleotide analogues. In another embodiment, the members of the array of oligonucleotide are arranged to present a moiety of interest within the oligonucleotide analogue probes of the array. For instance, the arrays are optionally conformationally restricted, having the formula $—X^{11}—Z—X^{12}$, wherein $X^{11}$ and $X^{12}$ are complementary oligonucleotides or oligonucleotide analogues and Z is a chemical structure comprising the binding site of interest.

Oligonucleotide analogue arrays are synthesized on a solid substrate by a variety of methods, including light-directed chemical coupling, and selectively flowing synthetic reagents over portions of the solid substrate. The solid substrate is prepared for synthesis or attachment of oligonucleotides by treatment with suitable reagents. For example, glass is prepared by treatment with silane reagents.

The present invention provides methods for determining whether a molecule of interest binds members of the oligonucleotide analogue array. For instance, in one embodiment, a target molecule is hybridized to the array and the resulting hybridization pattern is determined. The target molecule includes genomic DNA, cDNA, unspliced RNA, mRNA, and rRNA, nucleic acid analogues, proteins and chemical polymers. The target molecules are optionally amplified prior to being hybridized to the array, e.g., by PCR, LCR, or cloning methods.

The oligonucleotide analogue members of the array used in the above methods are synthesized by any described method for creating arrays. In one embodiment, the oligonucleotide analogue members are attached to the solid substrate, or synthesized on the solid substrate by light-directed very large scale immobilized polymer synthesis, e.g., using photo-removable protecting groups during synthesis. In another embodiment, the oligonucleotide members are attached to the solid substrate by forming a plurality of channels adjacent to the surface of said substrate, placing selected monomers in said channels to synthesize oligonucleotide analogues at predetermined portions of selected regions, wherein the portion of the selected regions comprise oligonucleotide analogues different from oligonucleotide analogues in at least one other of the selected regions, and repeating the steps with the channels formed along a second portion of the selected regions. The solid substrate is any suitable material as described above, including beads, slides, and arrays, each of which is constructed from, e.g., silica, polymers and glass.

DEFINITIONS

An "Oligonucleotide" is a nucleic acid sequence composed of two or more nucleotides. An oligonucleotide is optionally derived from natural sources, but is often synthesized chemically. It is of any size. An "oligonucleotide analogue" refers to a polymer with two or more monomeric subunits, wherein the subunits have some structural features in common with a naturally occurring oligonucleotide which allow it to hybridize with a naturally occurring oligonucleotide in solution. For instance, structural groups are optionally added to the ribose or base of a nucleoside for incorporation into an oligonucleotide, such as a methyl or allyl group at the 2'-O position on the ribose, or a fluoro group which substitutes for the 2'-O group, or a bromo group on the ribonucleoside base. The phosphodiester linkage, or "sugar-phosphate backbone" of the oligonucleotide analogue is substituted or modified, for instance with methyl phosphonates or O-methyl phosphates. Another example of an oligonucleotide analogue for purposes of this disclosure includes "peptide nucleic acids" in which native or modified nucleic acid bases are attached to a polyamide backbone. Oligonucleotide analogues optionally comprise a mixture of naturally occurring nucleotides and nucleotide analogues. However, an oligonucleotide which is made entirely of naturally occurring nucleotides (i.e., those comprising DNA or RNA), with the exception of a protecting group on the end of the oligonucleotide, such as a protecting group used during standard nucleic acid synthesis is not considered an oligonucleotide analogue for purposes of this invention.

A "nucleoside" is a pentose glycoside in which the aglycone is a heterocyclic base; upon the addition of a phosphate group the compound becomes a nucleotide. The major biological nucleosides are β-glycoside derivatives of D-ribose or D-2-deoxyribose. Nucleotides are phosphate esters of nucleosides which are generally acidic in solution due to the hydroxy groups on the phosphate. The nucleosides of DNA and RNA are connected together via phosphate units attached to the 3' position of one pentose and the 5' position of the next pentose. Nucleotide analogues and/or nucleoside analogues are molecules with structural similarities to the naturally occurring nucleotides or nucleosides as discussed above in the context of oligonucleotide analogues.

A "nucleic acid reagent" utilized in standard automated oligonucleotide synthesis typically caries a protected phosphate on the 3' hydroxyl of the ribose. Thus, nucleic acid reagents are referred to as nucleotides, nucleotide reagents, nucleoside reagents, nucleoside phosphates, nucleoside-3'-phosphates, nucleoside phosphoramidites, phosphoramidites, nucleoside phosphonates, phosphonates and the like. It is generally understood that nucleotide reagents carry a reactive, or activatible, phosphoryl or phosphonyl moiety in order to form a phosphodiester linkage.

A "protecting group" as used herein, refers to any of the groups which are designed to block one reactive site in a molecule while a chemical reaction is carried out at another reactive site. More particularly, the protecting groups used herein are optionally any of those groups described in Greene, et al., *Protective Groups In Organic Chemistry*, 2nd Ed., John Wiley & Sons, New York, NY, 1991, which is incorporated herein by reference. The proper selection of protecting groups for a particular synthesis is governed by the overall methods employed in the synthesis. For example, in "light-directed" synthesis, discussed herein, the protecting groups are photolabile protecting groups such as NVOC, MeNPoc, and those disclosed in co-pending Application PCT/US93/10162 (filed Oct. 22, 1993), incorporated herein by reference. In other methods, protecting groups are removed by chemical methods and include groups such as FMOC, DMT and others known to those of skill in the art.

A "purine" is a generic term based upon the specific compound "purine" having a skeletal structure derived from the fusion of a pyrimidine ring and an imidazole ring. It is generally, and herein, used to describe a generic class of compounds which have an atom or a group of atoms added to the parent purine compound, such as the bases found in the naturally occurring nucleic acids adenine (6-aminopurine) and guanine (2-amino-6-oxopurine), or less commonly occurring molecules such as 2-amino-adenine, $N^6$-methyladenine, or 2-methylguanine.

A "purine analogue" has a heterocyclic ring with structural similarities to a purine, in which an atom or group of atoms is substituted for an atom in the purine ring. For instance, in one embodiment, one or more N atoms of the purine heterocyclic ring are replaced by C atoms.

A "pyrimidine" is a compound with a specific heterocyclic diazine ring structure, but is used generically by persons of skill and herein to refer to any compound having a 1,3-diazine ring with minor additions, such as the common nucleic acid bases cytosine, thymine, uracil, 5-methylcytosine and 5-hydroxymethylcytosine, or the non-naturally occurring 5-bromo-uracil.

A "pyrimidine analogue" is a compound with structural similarity to a pyrimidine, in which one or more atom in the pyrimidine ring is substituted. For instance, in one embodiment, one or more of the N atoms of the ring are substituted with C atoms.

A "solid substrate" has fixed organizational support matrix, such as silica, polymeric materials, or glass. In some embodiments, at least one surface of the substrate is partially planar. In other embodiments it is desirable to physically separate regions of the substrate to delineate synthetic regions, for example with trenches, grooves, wells or the like. Example of solid substrates include slides, beads and arrays.

DESCRIPTION OF THE DRAWINGS

FIG. 1 shows four panels (FIG. 1A, FIG. 1B, FIG. 1C and FIG. 1D). FIGS. 1A and 1B graphically display the difference in fluorescence intensity between the matched and mismatched DNA probes.

DETAILED DESCRIPTION

Figure 1C:
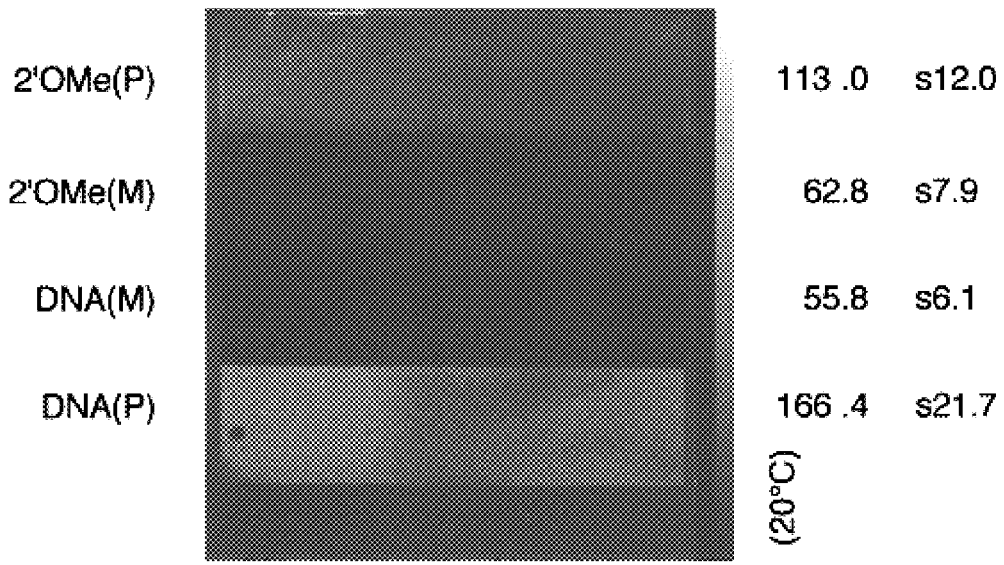
FIGS. 1C and 1D illustrate the difference in fluorescence intensity verses location on an example chip for DNA and RNA targets, respectively.

Methods of synthesizing desired single stranded oligonucleotide and oligonucleotide analogue sequences are known to those of skill in the art. In particular, methods of synthesizing oligonucleotides and oligonucleotide analogues are found in, for example, *Oligonucleotide Synthesis: A Practical Approach*, Gait, ed., IRL Press, Oxford (1984); W. H. A. Kuijpers *Nucleic Acids Research* 18(17), 5197 (1994); K. L. Dueholm *J. Org. Chem.* 59, 5767–5773 (1994), and S. Agrawal (ed.) *Methods in Molecular Biology*, volume 20, each of which is incorporated herein by reference in its entirety for all purposes. Synthesizing unimolecular double-stranded DNA in solution has also been described. See, copending application Ser. No. 08/327,687, now U.S. Pat. No. 5,556,752 which is incorporated herein for all purposes.

Improved methods of forming large arrays of oligonucleotides, peptides and other polymer sequences with a minimal number of synthetic steps are known. See, Pirrung et al., U.S. Pat. No. 5,143,854 (see also, PCT Application No. WO 90/15070) and Fodor et al., PCT Publication No. WO 92/10092, which are incorporated herein by reference, which disclose methods of forming vast arrays of peptides, oligonucleotides and other molecules using, for example, light-directed synthesis techniques. See also, Fodor et al., (1991) *Science*, 251, 767–77 which is incorporated herein by reference for all purposes. These procedures for synthesis of polymer arrays are now referred to as VLSIPS™ procedures.

Using the VLSIP™ approach, one heterogenous array of polymers is converted, through simultaneous coupling at a number of reaction sites, into a different heterogenous array. See, U.S. application Ser. No. 07/796,243 now U.S. Pat. No. 5,384,261 and U.S. application Ser. No. 07/980,523 now U.S. Pat. No. 5,677,195, the disclosures of which are incorporated herein for all purposes.

The development of VLSIPS™ technology as described in the above-noted U.S. Pat. No. 5,143,854 and PCT patent publication Nos. WO 90/15070 and 92/10092 is considered pioneering technology in the fields of combinatorial synthesis and screening of combinatorial libraries. More recently, patent application Ser. No. 08/082,937, filed Jun. 25, 1993 (incorporated herein by reference), describes methods for making arrays of oligonucleotide probes that are used to check or determine a partial or complete sequence of a target nucleic acid and to detect the presence of a nucleic acid containing a specific oligonucleotide sequence.

Combinatorial Synthesis of Oligonucleotide Arrays

VLSIPS™ technology provides for the combinatorial synthesis of oligonucleotide arrays. The combinatorial VLSIPS™ strategy allows for the synthesis of arrays containing a large number of related probes using a minimal number of synthetic steps. For instance, it is possible to synthesize and attach all possible DNA 8mer oligonucleotides ($4^8$, or 65,536 possible combinations) using only 32 chemical synthetic steps. In general, VLSIPS™ procedures provide a method of producing $4^n$ different oligonucleotide probes on an array using only 4n synthetic steps.

Figure 2:
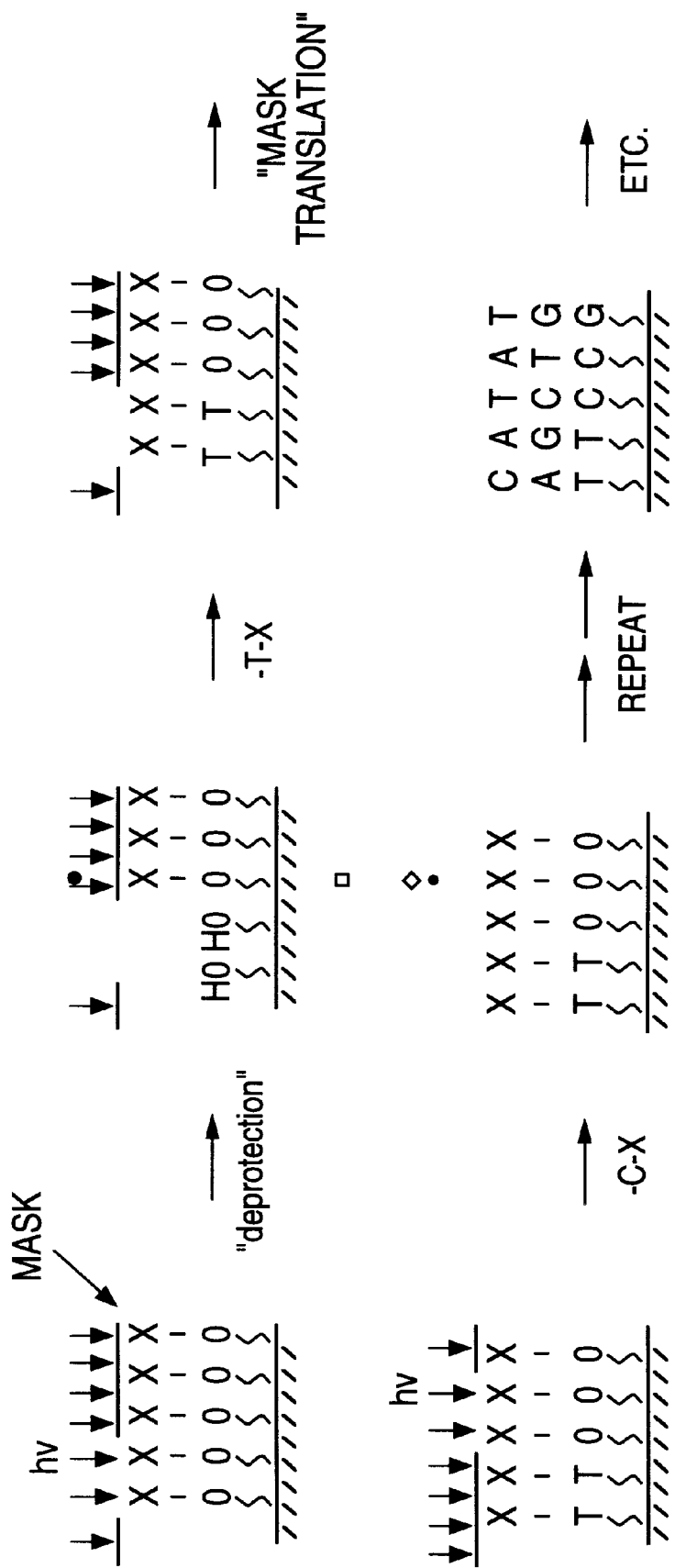
FIG. 2 is a graphic illustration of specific light-directed chemical coupling of oligonucleotide analogue monomers to an array.

In brief, the light-directed combinatorial synthesis of oligonucleotide arrays on a glass surface proceeds using automated phosphoramidite chemistry and chip masking techniques. In one specific implementation, a glass surface is derivatized with a silane reagent containing a functional group, e.g., a hydroxyl or amine group blocked by a photolabile protecting group. Photolysis through a photolithogaphic mask is used selectively to expose functional groups which are then ready to react with incoming 5'-photoprotected nucleoside phosphoramidites. See, FIG. 2. The phosphoramidites react only with those sites which are illuminated (and thus exposed by removal of the photolabile blocking group). Thus, the phosphoramidites only add to those areas selectively exposed from the preceding step. These steps are repeated until the desired array of sequences have been synthesized on the solid surface. Combinatorial synthesis of different oligonucleotide analogues at different locations on the array is determined by the pattern of illumination during synthesis and the order of addition of coupling reagents.

In the event that an oligonucleotide analogue with a polyamide backbone is used in the VLSIPS™ procedure, it is generally inappropriate to use phosphoramidite chemistry to perform the synthetic steps, since the monomers do not attach to one another via a phosphate linkage. Instead, peptide synthetic method are substituted. See, e.g., Pirrung et al. U.S. Pat. No. 5,143,854.

Peptide nucleic acids are commercially available from, e.g., Biosearch, Inc. (Bedford, Mass.) which comprise a polyamide backbone and the bases found in naturally occurring nucleosides. Peptide nucleic acids are capable of binding to nucleic acids with high specificity, and are considered "oligonucleotide analogues" for purposes of this disclosure. Note that peptide nucleic acids optionally comprise bases other than those which are naturally occurring.

Hybridization of Nucleotide Analogues

The stability of duplexes formed between RNAs or DNAs are generally in the order of RNA:RNA>RNA:DNA>DNA:DNA, in solution. Long probes have better duplex stability with a target, but poorer mismatch discrimination than shorter probes (mismatch discrimination refers to the measured hybridization signal ratio between a perfect match probe and a single base mismatch probe. Shorter probes (e.g., 8-mers) discriminate mismatches very well, but the overall duplex stability is low. In order to optimize mismatch discrimination and duplex stability, the present invention provides a variety of nucleotide analogues incorporated into polymers and attached in an array to a solid substrate.

Altering the thermal stability ($T_m$) of the duplex formed between the target and the probe using, e.g., known oligonucleotide analogues allows for optimization of duplex stability and mismatch discrimination. One useful aspect of altering the $T_m$ arises from the fact that Adenine-Thymine (A-T) duplexes have a lower $T_m$ than Guanine-Cytosine (G-C) duplexes, due in part to the fact that the A-T duplexes have 2 hydrogen bonds per base-pair, while the G-C duplexes have 3 hydrogen bonds per base pair. In heterogeneous oligonucleotide arrays in which there is a non-uniform distribution of bases, it can be difficult to optimize hybridization conditions for all probes simultaneously. Thus, in some embodiments, it is desirable to destabilize G-C-rich duplexes and/or to increase the stability of A-T-rich duplexes while maintaining the sequence specificity of hybridization. This is accomplished, e.g., by replacing one or more of the native nucleotides in the probe (or the target) with certain modified, non-standard nucleotides. Substitution of guanine residues with 7-deazaguanine, for example, will generally destabilize duplexes, whereas substituting adenine residues with 2,6-diaminopurine will enhance duplex stability. A variety of other modified bases are also incorporated into nucleic acids to enhance or decrease overall duplex stability while maintaining specificity of hybridization. The incorporation of 6-aza-pyrimidine analogs into oligonucleotide probes generally decreases their binding affinity for complementary nucleic acids. Many 5-substituted pyrimidines substantially increase the stability of hybrids in which they have been substituted in place of the native pyrimidines in the sequence. Examples include 5-bromo-, 5-methyl-, 5-propynyl-, 5-(imidazol-2-yl)-and 5-(thiazol-2-yl)-derivatives of cytosine and uracil.

Many modified nucleosides, nucleotides and various bases suitable for incorporation into nucleosides are commercially available from a variety of manufacturers, including the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), Invitrogen, San Diego, Calif., and Applied Biosystems (Foster City, Calif.), as well as many other commercial sources known to one of skill. Methods of attaching bases to sugar moieties to form nucleosides are known. See, e.g., Lukevics and Zablocka (1991), *Nucleoside Synthesis: Organosilicon Methods* Ellis Horwood Limited Chichester, West Sussex, England and the references therein. Methods of phosphorylating nucleosides to form nucleotides, and of incorporating nucleotides into oligonucleotides are also known. See, e.g., Agrawal (ed) (1993) *Protocols for Oligonucleotides and Analogues, Synthesis and Properties*, Methods in Molecular Biology volume 20, Humana Press, Towota, N.J., and the references therein. See also, Crooke and Lebleu, and Sanghvi and Cook, and the references cited therein, both supra.

Groups are also linked to various positions on the nucleoside sugar ring or on the purine or pyrimidine rings which may stabilize the duplex by electrostatic interactions with the negatively charged phosphate backbone, or through hydrogen bonding interactions in the major and minor groves. For example, adenosine and guanosine nucleotides are optionally substituted at the $N^2$ position with an imidazolyl propyl group, increasing duplex stability. Universal base analogues such as 3-nitropyrrole and 5-nitroindole are optionally included in oligonucleotide probes to improve duplex stability through base stacking interactions.

Selecting the length of oligonucleotide probes is also an important consideration when optimizing hybridization specificity. In general, shorter probe sequences are more specific than longer ones, in that the occurrence of a single-base mismatch has a greater destabilizing effect on the hybrid duplex. However, as the overall thermodynamic stability of hybrids decreases with length, in some embodiments it is desirable to enhance duplex stability for short probes globally. Certain modifications of the sugar moiety in oligonucleotides provide useful stabilization, and these can be used to increase the affinity of probes for complementary nucleic acid sequences. For example, 2'-O-methyl-, 2'-O-propyl-, and 2'-O-allyl-oligoribonucleotides have higher binding affinities for complementary RNA sequences than their unmodified counterparts. Probes comprised of 2'-fluoro-2'-deoxyollgoribonucleotides also form more stable hybrids with RNA than do their unmodified counterparts.

Replacement or substitution of the internucleotide phosphodiester linkage in oligo- or poly-nucleotides is also used to either increase or decrease the affinity of probe-target interactions. For example, substituting phosphodiester linkages with phosphorothioate or phosphorodithioate linkages generally lowers duplex stability, without affecting sequence specificity. Substitutions with a non-ionic methylphosphonate linkage (racemic, or preferably, Rp stereochemistry) have a stabilizing influence on hybrid formation. Neutral or cationic phosphoramidate linkages also result in enhanced duplex stabilization. The phosphate diester backbone has been replaced with a variety of other stabilizing, non-natural linkages which have been studied as potential antisense therapeutic agents. See, e.g., Crooke and Lebleu (eds) (1993) *Antisense Research Applications* CRC Press; and, Sanghvi and Cook (eds) (1994) *Carbohydrate modifications in Antisense Research* ACS Symp. Ser. #580 ACS, Washington DC. Very stable hybrids are formed between nucleic acids and probes comprised of peptide nucleic acids, in which the entire sugar-phosphate backbone has been replaced with a polyamide structure.

Another important factor which sometimes affects the use of oligonucleotide probe arrays is the nature of the target nucleic acid. Oligodeoxynucleotide probes can hybridize to DNA and RNA targets with different affinity and specificity. For example, probe sequences containing long "runs" of consecutive deoxyadenosine residues form less stable hybrids with complementary RNA sequences than with the complementary DNA sequences. Substitution of dA in the probe with either 2,6-diaminopurine deoxyriboside, or 2'-alkoxy- or 2'-fluoro-dA enhances hybridization with RNA targets.

Internal structure within nucleic acid probes or the targets also influences hybridization efficiency. For example, GC-rich sequences, and sequences containing "runs" of consecutive G residues frequently self-associate to form higher-order structures, and this can inhibit their binding to complementary sequences. See, Zimmermann et al. (1975) *J. Mol Biol* 92: 181; Kim (1991) *Nature* 351: 331; Sen and Gilbert (1988) *Nature* 335: 364; and Sunquist and Klug (1989) *Nature* 342: 825. These structures are selectively destabilized by the substitution of one or more guanine residues with one or more of the following purines or purine analogs: 7-deazaguanine, 8-aza-7-deazaguanine, 2-aminopurine, 1H-purine, and hypoxanthine, in order to enhance hybridization.

Modified nucleic acids and nucleic acid analogs can also be used to improve the chemical stability of probe arrays. For example, certain processes and conditions that are useful for either the fabrication or subsequent use of the arrays, may not be compatible with standard oligonucleotide chemistry, and alternate chemistry can be employed to overcome these problems. For example, exposure to acidic conditions will cause depurination of purine nucleotides, ultimately resulting in chain cleavage and overall degradation of the probe array. In this case, adenine and guanine are replaced with 7-deazaadenine and 7-deazaguanine, respectively, in order to stabilize the oligonucleotide probes towards acidic conditions which are used during the manufacture or use of the arrays.

Base, phosphate and sugar modifications are used in combination to make highly modified oligonucleotide analogues which take advantage of the properties of each of the various modifications. For example, oligonucleotides which have higher binding affinities for complementary sequences than their unmodified counterparts (e.g., 2'-O-methyl-, 2'-O-propyl-, and 2'-O-allyl oligonucleotides) can be incorporated into oligonucleotides with modified bases (deazaguanine, 8-aza-7-deazaguanine, 2-aminopurine, 1H-purine, hypoxanthine and the like) with non-ionic methylphosphonate linkages or neutral or cationic phosphoramidate linkages, resulting in additive stabilization of duplex formation between the oligonucleotide and a target nucleic acid. For instance, one preferred oligonucleotide comprises a 2'-O-methyl-2,6-diaminopurineriboside phosphorothioate. Similarly, any of the modified bases described herein can be incorporated into peptide nucleic acids, in which the entire sugar-phosphate backbone has been replaced with a polyamide structure.

Thermal equilibrium studies, kinetic "on-rate" studies, and sequence specificity analysis is optionally performed for any target oligonucleotide and probe or probe analogue. The data obtained shows the behavior of the analogues upon duplex formation with target oligonucleotides. Altered duplex stability conferred by using oligonucleotide analogue probes are ascertained by following, e.g., fluorescence signal intensity of oligonucleotide analogue arrays hybridized with a target oligonucleotide over time. The data allow optimization of specific hybridization conditions at, e.g., room temperature (for simplified diagnostic applications).

Another way of verifying altered duplex stability is by following the signal intensity generated upon hybridization with time. Previous experiments using DNA targets and DNA chips have shown that signal intensity increases with time, and that the more stable duplexes generate higher signal intensities faster than less stable duplexes. The signals reach a plateau or "saturate" after a certain amount of time due to all of the binding sites becoming occupied. These data allow for optimization of hybridization, and determination of equilibration conditions at a specified temperature.

Graphs of signal intensity and base mismatch positions are plotted and the ratios of perfect match versus mismatches calculated. This calculation shows the sequence specific properties of nucleotide analogues as probes. Perfect match/mismatch ratios greater than 4 are often desirable in an oligonucleotide diagnostic assay because, for a diploid genome, ratios of 2 have to be distinguished (e.g., in the case of a heterozygous trait or sequence).

Target Nucleic Acids Which Comprise Nucleotide Analogues

Modified nucleotides and nucleotide analogues are incorporated synthetically or enzymatically into DNA or RNA target nucleic acids for hybridization analysis to oligonucleotide arrays. The incorporation of nucleotide analogues in the target optimizes the hybridization of the target in terms of sequence specificity and/or the overall affinity of binding to oligonucleotide and oligonucleotide analogue probe arrays. The use of nucleotide analogues in either the oligonucleotide array or the target nucleic acid, or both, improves optimizability of hybridization interactions. Examples of useful nucleotide analogues which are substituted for naturally occurring nucleotides include 7-deazaguanosine, 2,6-diaminopurine nucleotides, 5-propynyl and other 5-substituted pyrimidine nucleotides, 2'-fluro and 2'-methoxy -2'-deoxynucleotides and the like.

These nucleotide analogues are incorporated into nucleic acids using the synthetic methods described supra, or using DNA or RNA polymerases. The nucleotide analogues are preferably incorporated into target nucleic acids using in vitro amplification methods such as PCR, LCR, Qβ-replicase expansion, in vitro transcription (e.g., nick translation or random-primer transcription) and the like. Alternatively, the nucleotide analogues are optionally incorporated into cloned nucleic acids by culturing a cell which comprises the cloned nucleic acid in media which includes a nucleotide analogue.

Similar to the use of nucleotide analogues in probe arrays, 7-deazaguanosine is used in target nucleic acids to substitute for G/dG to enhance target hybridization by reducing secondary structure in sequences containing runs of poly-G/dG. 6diaminopurine nucleotides substitute for A/dA to enhance target hybridization through enhanced H-bonding to T or U rich probes. 5-propynyl and other 5-substituted pyrimidine nucleotides substitute for natural pyrimidines to enhance target hybridization to certain purine rich probes. 2'-fluro and 2'-methoxy-2'-deoxynucleotides substitute for natural nucleotides to enhance target hybridization to similarly substituted probe sequences.

Synthesis of 5'-photoprotected 2'-O alkyl ribonucleotide analogues

The light-directed synthesis of complex arrays of nucleotide analogues on a glass surface is achieved by derivatizing cyanoethyl phosphoramidite nucleotides and nucleotide analogues (e.g., nucleoside analogues of uridine, thymidine, cytidine, adenosine and guanosine, with phosphates) with, for example, the photolabile MeNPoc group in the 5'-hydroxyl position instead of the usual dimethoxytrityl group. See, application SN PCT/US94/12305.

Specific base-protected 2'-O alkyl nucleosides are commercially available, from, e.g., Chem Genes Corp. (MA). The photolabile MeNPoc group is added to the 5'-hydroxyl position followed by phosphitylation to yield cyanoethyl phosphoramidite monomers. Commercially available nucleosides are optionally modified (e.g., by 2-O-alkylation) to create nucleoside analogues which are used to generate oligonucleotide analogues.

Modifications to the above procedures are used in some embodiments to avoid significant addition of MenPoc to the 3'-hydroxyl position. For instance, in one embodiment, a 2'-O-methyl ribonucleotide analogue is reacted with DMT-Cl {di(p-methoxyphenyl)phenylchloride} in the presence of pyridine to generate a 2'-O-methyl-5'-O-DMT ribonucleotide analogue. This allows for the addition of TBDMS to the 3'-O of the ribonucleoside analogue by reaction with TBDMS-Triflate (t-butyldimethylsilyltrifluoromethanesulfonate) in the presence of triethylamine in THF (tetrahydrofuran) to yield a 2'-O-methyl-3'-O-TBDMS-5'-O-DMT ribonucleotide base analogue. This analogue is treated with TCAA (trichloroacetic acid) to cleave off the DMT group, leaving a reactive hydroxyl group at the 5' position. MeNPoc is then added to the oxygen of the 5' hydroxyl group using MenPoc-Cl in the presence of pyridine. The TBDMS group is then cleaved with F⁻ (e.g., NaF) to yield a ribonucleotide base analogue with a MeNPoc group attached to the 5' oxygen on the nucleotide analogue. If appropriate, this analogue is phosphitylated to yield a phosphoramidite for oligonucleotide analogue synthesis. Other nucleosides or nucleoside analogues are protected by similar procedures.

Synthesis of Oligonucleotide Analogue Arrays on Chips

Other than the use of photoremovable protecting groups, the nucleoside coupling chemistry used in VLSIPS™ technology for synthesizing oligonucleotides and oligonucleotide analogues on chips is similar to that used for oligonucleotide synthesis. The oligonucleotide is typically linked to the substrate via the 3'-hydroxyl group of the oligonucleotide and a functional group on the substrate which results in the formation of an ether, ester, carbamate or phosphate ester linkage. Nucleotide or oligonucleotide analogues are attached to the solid support via carbon-carbon bonds using, for example, supports having (poly)trifluorochloroethylene surfaces, or preferably, by siloxane bonds (using, for example, glass or silicon oxide as the solid support). Siloxane bonds with the surface of the support are formed in one embodiment via reactions of surface attaching portions bearing trichlorosilyl or trialkoxysilyl groups. The surface attaching groups have a site for attachment of the oligonucleotide analogue portion. For example, groups which are suitable for attachment include amines, hydroxyl, thiol, and carboxyl. Preferred surface attaching or derivitizing portions include aminoalkylsilanes and hydroxyalkylsilanes. In particularly preferred embodiments, the surface attaching portion of the oligonucleotide analogue is either bis(2-hydroxyethyl)-aminopropyltriethoxysilane, n-(3-triethoxysilylpropyl)-4-hydroxybutylamide, aminopropyltriethoxysilane or hydroxypropyltriethoxysilane.

The oligoribonucleotides generated by synthesis using ordinary ribonucleotides are usually base labile due to the presence of the 2'-hydroxyl group. 2'-O-methyloligoribonucleotides (2'-OMeORNs), analogues of RNA where the 2'-hydroxyl group is methylated, are DNAse and RNAse resistant, making them less base labile. Sproat, B. S., and Lamond, A. I. in *Oligonucleotides and Analogues: A Practical Approach*, edited by F. Eckstein, New York: IRL Press at Oxford University Press, 1991, pp. 49–86, incorporated herein by reference for all purposes, have reported the synthesis of mixed sequences of 2'-O-Methoxy-oligoribonucleotides (2'-O-MeORNs) using dimethoxytrityl phosphoramidite chemistry. These 2'-O-MeORNs display greater binding affinity for complementary nucleic acids than their unmodified counterparts.

Other embodiments of the invention provide mechanical means to generate oligonucleotide analogues. These techniques are discussed in co-pending application Ser. No. 07/796,243, filed Nov. 22, 1991, which is incorporated herein by reference in its entirety for all purposes. Essentially, oligonucleotide analogue reagents are directed over the surface of a substrate such that a predefined array of oligonucleotide analogues is created. For instance, a series of channels, grooves, or spots are formed on or adjacent to a substrate. Reagents are selectively flowed through or deposited in the channels, grooves, or spots, forming an array having different oligonucleotides and/or oligonucleotide analogues at selected locations on the substrate.

Detection of Hybridization

In one embodiment, hybridization is detected by labeling a target with, e.g., fluorescein or other known visualization agents and incubating the target with an array of oligonucleotide analogue probes. Upon duplex formation by the target with a probe in the array (or triplex formation in embodiments where the array comprises unimolecular double-stranded probes), the fluorescein label is excited by, e.g., an argon laser and detected by viewing the array, e.g., through a scanning confocal microscope.

Sequencing by hybridization

Current sequencing methodologies are highly reliant on complex procedures and require substantial manual effort. Conventional DNA sequencing technology is a laborious procedure requiring electrophoretic size separation of labeled DNA fragments. An alternative approach involves a hybridization strategy carried out by attaching target DNA to a surface. The target is interrogated with a set of oligonucleotide probes, one at a time (see, application SN PCT/US94/12305).

A preferred method of oligonucleotide probe array synthesis involves the use of light to direct the synthesis of oligonucleotide analogue probes in high-density, miniaturized arrays. Matrices of spatially-defined oligonucleotide analogue probe arrays were generated. The ability to use these arrays to identify complementary sequences was demonstrated by hybridizing fluorescent labeled oligonucleotides to the matrices produced.

Oligonucleotide analogue arrays are used, e.g., to study sequence specific hybridization of nucleic acids, or protein-nucleic acid interactions. Oligonucleotide analogue arrays are used to define the thermodynamic and kinetic rules governing the formation and stability of oligonucleotide and oligonucleotide analogue complexes.

Oligonucleotide analogue Probe Arrays and Libraries

The use of oligonucleotide analogues in probe arrays provides several benefits as compared to standard oligonucleotide arrays. For instance, as discussed supra, certain oligonucleotide analogues have enhanced hybridization characteristics to complementary nucleic acids as compared with oligonucleotides made of naturally occurring nucleotides. One primary benefit of enhanced hybridization characteristics is that oligonucleotide analogue probes are optionally shorter than corresponding probes which do not include nucleotide analogues.

Standard oligonucleotide probe arrays typically require fairly long probes (about 15–25 nucleotides) to achieve strong binding to target nucleic acids. The use of such long probes is disadvantageous for two reasons. First, the longer the probe, the more synthetic steps must be performed to make the probe and any probe array comprising the probe. This increases the cost of making the probes and arrays. Furthermore, as each synthetic step results in less than 100% coupling for every nucleotide, the quality of the probes degrades as they become longer. Secondly, short probes provide better mis-match discrimination for hybridization to a target nucleic acid. This is because a single base mismatch for a short probe-target hybridization is less destabilizing than a single mismatch for a long probe-target hybridization. Thus, it is harder to distinguish a single probe-target mismatch when the probe is a 20-mer than when the probe is an 8-mer. Accordingly, the use of short oligonucleotide analogue probes reduces costs and increases mismatch discrimination in probe arrays.

The enhanced hybridization characteristics of oligonucleotide analogues also allows for the creation of oligonucleotide analogue probe arrays where the probes in the arrays have substantial secondary structure. For instance, the oligonucleotide analogue probes are optionally configured to be fully or partially double stranded on the array. The probes are optionally complexed with complementary nucleic acids, or are optionally unimolecular oligonucleotides with self-complementary regions. Libraries of diverse double-stranded oligonucleotide analogue probes are used, for example, in screening studies to determine binding affinity of nucleic acid binding proteins, drugs, or oligonucleotides (e.g., to examine triple helix formation). Specific oligonucleotide analogues are known to be conducive to the formation of unusual secondary structure. See, Durland (1995) *Bioconjugate Chem.* 6: 278–282. General strategies for using unimolecular double-stranded oligonucleotides as probes and for library generation is described in application Ser. No 08/327,687, and similar strategies are applicable to oligonucleotide analogue probes.

In general, a solid support, which optionally has an attached spacer molecule is attached to the distal end of the oligonucleotide analogue probe. The probe is attached as a single unit, or synthesized on the support or spacer in a monomer by monomer approach using the VLSIPS™ or mechanical partitioning methods described supra. Where the oligonucleotide analogue arrays are fully double-stranded, oligonucleotides (or oligonucleotide analogues) complementary to the probes on the array are hybridized to the array.

In some embodiments, molecules other than oligonucleotides, such as proteins, dyes, co-factors, linkers and the like are incorporated into the oligonucleotide analogue probe, or attached to the distal end of the oligomer, e.g., as a spacing molecule, or as a probe or probe target. Flexible linkers are optionally used to separate complementary portions of the oligonucleotide analogue.

The present invention also contemplates the preparation of libraries of oligonucleotide analogues having bulges or loops in addition to complementary regions. Specific RNA bulges are often recognized by proteins (e.g., TAR RNA is recognized by the TAT protein of HIV). Accordingly, libraries of oligonucleotide analogue bulges or loops are useful in a number of diagnostic applications. The bulge or loop can be present in the oligonucleotide analogue or linker portions.

Unimolecular analogue probes can be configured in a variety of ways. In one embodiment, the unimolecular probes comprise linkers, for example, where the probe is arranged according to the formula Y—$L^1$—$X^1$—$L^2$—$X^2$, in which Y represents a solid support, $X^1$ and $X^2$ represent a pair of complementary oligonucleotides or oligonucleotide analogues, $L^1$ represents a bond or a spacer, and $L^2$ represents a linking group having sufficient length such that $X^1$ and $X^2$ form a double-stranded oligonucleotide. The general synthetic and conformational strategy used in generating the double-stranded unimolecular probes is similar to that described in co-pending application Ser. No. 08/327,687, except that any of the elements of the probe ($L^1$, $X^1$, $L^2$ and $X^2$) comprises a nucleotide or an oligonucleotide analogue. For instance, in one embodiment $X^1$ is an oligonucleotide analogue.

The oligonucleotide analogue probes are optionally arranged to present a variety of moieties. For example, structural components are optionally presented from the middle of a conformationally restricted oligonucleotide analogue probe. In these embodiments, the analogue probes generally have the structure—$X^1$—Z—$X^2$ wherein $X^{11}$ and $X^{12}$ are complementary oligonucleotide analogues and Z is a structural element presented away from the surface of the probe array. Z can include an agonist or antagonist for a cell membrane receptor, a toxin, venom, viral epitope, hormone, peptide, enzyme, cofactor, drug, protein, antibody or the like.

General tiling strategies for detection of a Polymorphism in a target oligonucleotide In diagnostic applications, oligonucleotide analogue arrays (e.g., arrays on chips, slides or beads) are used to determine whether there are any differences between a reference sequence and a target oligonucleotide, e.g., whether an individual has a mutation or polymorphism in a known gene. As discussed supra, the oligonucleotide target is optionally a nucleic acid such as a PCR amplicon which comprises one or more nucleotide analogues. In one embodiment, arrays are designed to contain probes exhibiting complementarity to one or more selected reference sequence whose sequence is known. The arrays are used to read a target sequence comprising either the reference sequence itself or variants of that sequence. Any polynucleotide of known sequence is selected as a reference sequence. Reference sequences of interest include sequences known to include mutations or polymorphisms associated with phenotypic changes having clinical significance in human patients. For example, the CFTR gene and P53 gene in humans have been identified as the location of several mutations resulting in cystic fibrosis or cancer respectively. Other reference sequences of interest include those that serve to identify pathogenic microorganisms and/or are the site of mutations by which such microorganisms acquire drug resistance (e.g., the HIV reverse transcriptase gene for HIV resistance). Other reference sequences of interest include regions where polymorphic variations are known to occur (e.g., the D-loop region of mitochondrial DNA). These reference sequences also have utility for, e.g., forensic, cladistic, or epidemiological studies.

Other reference sequences of interest include those from the genome of pathogenic viruses (e.g., hepatitis (A, B, or C), herpes virus (e.g., VZV, HSV-1, HAV-6, HSV-II, CMV, and Epstein Barr virus), adenovirus, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus. Other reference sequences of interest are from genomes or episomes of pathogenic bacteria, particularly regions that confer drug resistance or allow phylogenic characterization of the host (e.g., 16S rRNA or corresponding DNA). For example, such bacteria include chlamydia, rickettsial bacteria, mycobacteria, staphylococci, treptocci, pneumonococci, meningococci and conococci, klebsiella, proteus, serratia, pseudomonas, legionella, diphtheria, salmonella, bacilli, cholera, tetanus, botulism, anthrax, plague, leptospirosis, and Lymes disease bacteria. Other reference sequences of interest include those in which mutations result in the following autosomal recessive disorders: sickle cell anemia, β-thalassemia, phenylketonuria, galactosemia, Wilson's disease, hemochromatosis, severe combined immunodeficiency, alpha-1-antitrypsin deficiency, albinism, alkaptonuria, lysosomal storage diseases and Ehlers-Danlos syndrome. Other reference sequences of interest include those in which mutations result in X-linked recessive disorders: hemophilia, glucose-6-phosphate dehydrogenase, agammaglobulimenia, diabetes insipidus, Lesch-Nyhan syndrome, muscular dystrophy, Wiskott-Aldrich syndrome, Fabry's disease and fragile X-syndrome. Other reference sequences of interest includes those in which mutations result in the following autosomal dominant disorders: familial hypercholesterolemia, polycystic kidney disease, Huntington's disease, hereditary spherocytosis, Marfan's syndrome, von Willebrand's disease, neurofibromatosis, tuberous sclerosis, hereditary hemorrhagic telangiectasia, familial colonic polyposis, Ehlers-Danlos syndrome, myotonic dystrophy, muscular dystrophy, osteogenesis imperfecta, acute intermittent porphyria, and von Hippel-Lindau disease.

Although an array of oligonucleotide analogue probes is usually laid down in rows and columns for simplified data processing, such a physical arrangement of probes on the solid substrate is not essential. Provided that the spatial location of each probe in an array is known, the data from the probes is collected and processed to yield the sequence of a target irrespective of the physical arrangement of the probes on, e.g., a chip. In processing the data, the hybridization signals from the respective probes is assembled into any conceptual array desired for subsequent data reduction, whatever the physical arrangement of probes on the substrate.

In one embodiment, a basic tiling strategy provides an array of immobilized probes for analysis of a target oligonucleotide showing a high degree of sequence similarity to one or more selected reference oligonucleotide (e.g., detection of a point mutation in a target sequence). For instance, a first probe set comprises a plurality of probes exhibiting perfect complementarity with a selected reference oligonucleotide. The perfect complementarity usually exists throughout the length of the probe. However, probes having a segment or segments of perfect complementarity that is/are flanked by leading or trailing sequences lacking complementarity to the reference sequence can also be used. Within a segment of complementarity, each probe in the first probe set has at least one interrogation position that corresponds to a nucleotide in the reference sequence. The interrogation position is aligned with the corresponding nucleotide in the reference sequence when the probe and reference sequence are aligned to maximize complementarity between the two. If a probe has more than one interrogation position, each corresponds with a respective nucleotide in the reference sequence. The identity of an interrogation position and corresponding nucleotide in a particular probe in the first probe set cannot be determined simply by inspection of the probe in the first set. An interrogation position and corresponding nucleotide is defined by the comparative structures of probes in the first probe set and corresponding probes from additional probe sets.

For each probe in the first set, there are, for purposes of the present illustration, multiple corresponding probes from additional probe sets. For instance, there are optionally probes corresponding to each nucleotide of interest in the reference sequence. Each of the corresponding probes has an interrogation position aligned with that nucleotide of interest. Usually, the probes from the additional probe sets are identical to the corresponding probe from the first probe set with one exception. The exception is that at the interrogation position, which occurs in the same position in each of the corresponding probes from the additional probe sets. This position is occupied by a different nucleotide in the corresponding probe sets. Other tiling strategies are also employed, depending on the information to be obtained.

The probes are oligonucleotide analogues which are capable of hybridizing with a target nucleic sequence by complementary base-pairing. Complementary base pairing includes sequence-specific base pairing, which comprises, e.g., Watson-Crick base pairing or other forms of base pairing such as Hoogsteen base pairing. The probes are attached by any appropriate linkage to a support. 3' attachment is more usual as this orientation is compatible with the preferred chemistry used in solid phase synthesis of oligonucleotides and oligonucleotide analogues (with the exception of, e.g., analogues which do not have a phosphate backbone, such as peptide nucleic acids).

EXAMPLES

The following examples are provided by way of illustration only and not by way of limitation. A variety of parameters can be changed or modified to yield essentially similar results.

One approach to enhancing oligonucleotide hybridization is to increase the thermal stability ($T_m$) of the duplex formed between the target and the probe using oligonucleotide analogues that are known to increase $T_m$'s upon hybridization to DNA. Enhanced hybridization using oligonucleotide analogues is described in the examples below, including enhanced hybridization in oligonucleotide arrays.

Example 1

Solution oligonucleotide melting $T_m$

The $T_m$ of 2'-O-methyl oligonucleotide analogues was compared to the $T_m$ for the corresponding DNA and RNA sequences in solution. In addition, the $T_m$ of 2'-O-methyl oligonucleotide:DNA, 2'-O-methyl oligonucleotide:RNA and RNA:DNA duplexes in solution was also determined.

The $T_m$ was determined by varying the sample temperature and monitoring the absorbance of the sample solution at 260 nm. The oligonucleotide samples were dissolved in a 0.1M NaCl solution with an oligonucleotide concentration of 2 µM. Table 1 summarizes the results of the experiment. The results show that the hybridization of DNA in solution has approximately the same $T_m$ as the hybridization of DNA with a 2'-O-methyl-substituted oligonucleotide analogue. The results also show that the $T_m$ for the 2'-O-methyl-substituted oligonucleotide duplex is higher than that for the corresponding RNA:2'-O-methyl-substituted oligonucleotide duplex, which is higher than the $T_m$ for the corresponding DNA:DNA or RNA:DNA duplex.

TABLE 1

Solution Oligonucleotide Melting Experiments
(+) = Target Sequence
(5'-CTGAACGGTAGCATCTTGAC-3')(SEQ ID NO: 6)*
(−) = Complementary Sequence
(5'GTCAAGATGCTACCGTTCAG-3')(SEQ ID NO: 7)*

| Type of Oligonucleotide, Target Sequence (+) | Type of Oligonucleotide, Complementary Sequence (+) | $T_m$ (° C.) |
|---|---|---|
| DNA(+) | DNA(−) | 61.6 |
| DNA(+) | 2'OMe(−) | 58.6 |
| 2'OMe(+) | DNA(−) | 61.6 |
| 2'OMe(+) | 2'OMe(−) | 78.0 |
| RNA(+) | DNA(−) | 58.2 |
| RNA(+) | 2'OMe(−) | 73.6 |

*T refers to thymine for the DNA oligonucleotides, or uracil for the RNA oligonucleotides.

Example 2

Array hybridization experiments with DNA chips and oligonucleotide analogue targets A variable length DNA probe array on a chip was designed to discriminate single base mismatches in the 3 corresponding sequences 5'-CTGAACGGTAGCATCTTGAC-3' (SEQ ID NO:6) (DNA target), 5'-CUGAACGGUAGCAUCUUGAC-3' (SEQ ID NO:8) (RNA target) and 5'-CUGAACGGUAGCAUCUUGAC-3' (SEQ ID NO:9) (2'-O-methyl oligonucleotide target), and generated by the VLSIPS™ procedure. The Chip was designed with adjacent 12-mers and 8-mers which overlapped with the 3 target sequences as shown in Table 2.

TABLE 2

Array hybridization Experiments

| | |
|---|---|
| Target 1 (DNA) | 5'-CTGAACGGTAGCATCTTGAC-3' (SEQ ID NO: 6) |
| 8-mer probe (complement) | |
| 12-mer probe (complement) | |
| Target 2 (RNA) | 5'-CUGAACGGUAGCAUCUUGAC-3' (SEQ ID NO: 8) |
| 8-mer probe (complement) | |
| 12-mer probe (complement) | |
| Target 3 (2'-O-Me oligo) | 5'-CUGAACGGUAGCAUCUUGAC-3' (SEQ ID NO: 9) |
| 8-mer probe (complement) | |
| 12-mer probe (complement) | |

Target oligos were synthesized using standard techniques. The DNA and 2'-O-methyl oligonucleotide analogue target oligonucleotides were hybridized to the chip at a concentration of 10 nM in 5× SSPE at 20° C. in sequential experiments. Intensity measurements were taken at each probe position in the 8-mer and 12-mer arrays over time. The rate of increase in intensity was then plotted for each probe position. The rate of increase in intensity was similar for both targets in the 8-mer probe arrays, but the 12-mer probes hybridized more rapidly to the DNA target oligonucleotide.

Plots of intensity versus probe position were generated for the RNA, DNA and 2-O-methyl oligonucleotides to ascertain mismatch discrimination. The 8-mer probes displayed similar mismatch discrimination against all targets. The 12-mer probes displayed the highest mismatch discrimination for the DNA targets, followed by the 2'-O-methyl target, with the RNA target showing the poorest mismatch discrimination.

Thermal equilibrium experiments were performed by hybridizing each of the targets to the chip for 90 minutes at 5° C. temperature intervals. The chip was hybridized with the target in 5× SSPE at a target concentration of 10 nM. Intensity measurements were taken at the end of the 90 minute hybridization at each temperature point as described above. All of the targets displayed similar stability, with minimal hybridization to the 8-mer probes at 30° C. In addition, all of the targets showed similar stability in hybridizing to the 12-mer probes. Thus, the 2'-O-methyl oligonucleotide target had similar hybridization characteristics to DNA and RNA targets when hybridized against DNA probes.

Example 3

2'-O-methyl-substituted oligonucleotide chips

DMT-protected DNA and 2'-O-methyl phosphoramidites were used to synthesize 8-mer probe arrays on a glass slide using the VLSIPS™ method. The resulting chip was hybridized to DNA and RNA targets in separate experiments. The target sequence, the sequences of the probes on the chip and the general physical layout of the chip is described in Table 3.

Figure 1D:
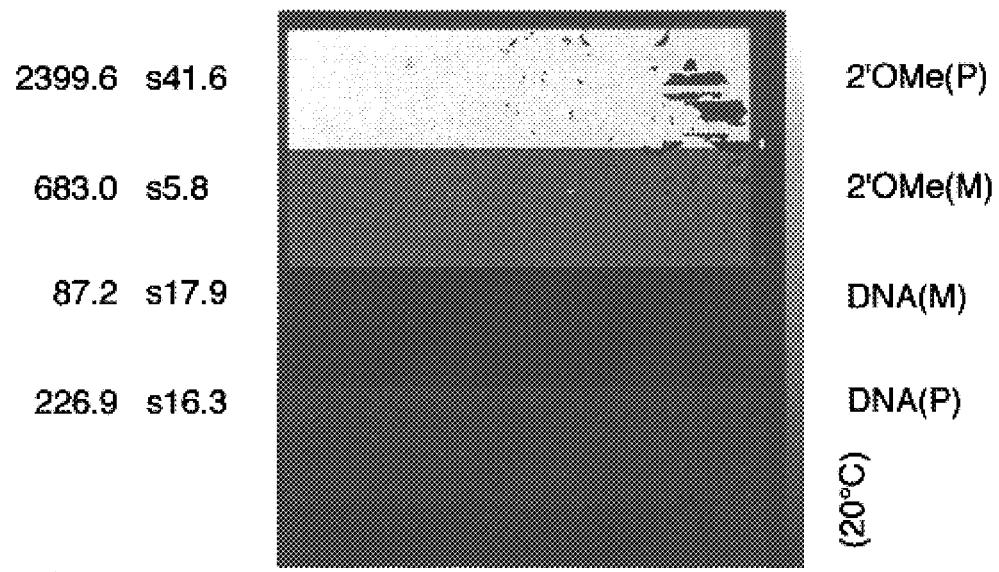

The chip was hybridized to the RNA and DNA targets in successive experiments. The hybridization conditions used were 10 nM target, in 5× SSPE. The chip and solution were heated from 20° C. to 50° C., with a fluorescence measurement taken at 5 degree intervals as described in SN PCT/US94/12305. The chip and solution were maintained at each temperature for 90 minutes prior to fluorescence measurements. The results of the experiment showed that DNA probes were equal or superior to 2'-O-methyl oligonucleotide analogue probes for hybridization to a DNA target, but that the 2'-O-methyl analogue oligonucleotide probes showed dramatically better hybridization to the RNA target than the DNA probes. In addition, the 2'-O-methyl analogue oligonucleotide probes showed superior mismatch discrimination of the RNA target compared to the DNA probes. The difference in fluorescence intensity between the matched and mismatched analogue probes was greater than the difference between the matched and mismatched DNA probes, dramatically increasing the signal-to-noise ratio. FIG. 1 displays the results graphically (FIGS. 1A and 1B). (M) and (P) indicate mismatched and perfectly matched probes, respectively. (FIGS. 1C and 1D) illustrates the fluorescence intensity versus location on an example chip for the various probes at 20° C. using DNA and RNA targets, respectively.

TABLE 3

2'-O-methyl Oligonucleotide Analogues on a Chip.

| | |
|---|---|
| Target Sequence (DNA): | 5'-CTGAACGGTAGCATCTTGAC-3' (SEQ ID NO: 6) |
| Target Sequence (RNA): | 5'-CUGAACGGUAGCAUCUUGAC-3' (SEQ ID NO: 8) |
| Matching DNA oligonucleotide probe {DNA (M)} | 5'-CTTGCCAT (SEQ ID NO: 10) |
| Matching 2'-O-methyl oligonucleotide analogue probe {2'OMe (M)} | 5'-CUUGCCAU (SEQ ID NO: 11) |
| DNA oligonucleotide probe with 1 base mismatch {DNA (P)} | 5'-CTTGCTAT (SEQ ID NO: 12) |
| 2'-O-methyl oligonucleotide analogue probe with 1 base mismatch {2'OMe (M)} | 5'-CUUGCUAU (SEQ ID NO: 13) |

SCHEMATIC REPRESENTATION OF 2'-O-METHYL/DNA CHIP

Matching 2'-O-methyl oligonucleotide analogue probe
2'-O-methyl oligonucleotide analogue probe with 1 base mismatch
DNA oligonucleotide probe with 1 base mismatch
Matching DNA oligonucleotide probe Example 4

Synthesis of oligonucleotide analogues

The reagent MeNPoc-Cl group reacts non-selectively with both the 5' and 3' hydroxyls on 2'-O-methyl nucleoside analogues. Thus, to generate high yields of 5'-O-MeNPoc-2'-O-methylribonucleoside analogues for use in oligonucleotide analogue synthesis, the following protection-deprotection scheme was utilized.

The protective group DMT was added to the 5'-O position of the 2'-O-methylribonucleoside analogue in the presence of pyridine. The resulting 5'-O-DMT protected analogue was reacted with TBDMS-Triflate in THF, resulting in the addition of the TBDMS group to the 3'-O of the analogue. The 5'-DMT group was then removed with TCAA to yield a free OH group at the 5' position of the 2'-O-methyl ribonucleoside analogue, followed by the addition of MeNPoc-Cl in the presence of pyridine, to yield 5'-O-MeNPoc-3'-O-TBDMS-2'-O-methyl ribonucleoside analogue. The TBDMS group was then removed by reaction with NaF, and the 3'-OH group was phosphitylated using standard techniques.

Two other potential strategies did not result in high specific yields of 5'-O-MeNPoc-2'-O-methylribonucleoside. In the first, a less reactive MeNPoc derivative was synthesized by reacting MeNPoc-Cl with N-hydroxy succimide to yield MeNPoc-NHS. This less reactive photocleavable group (MeNPoc-NHS) was found to react exclusively with the 3' hydroxyl on the 2'-O-methylribonucleoside analogue. In the second strategy, an organotin protection scheme was used. Dibutyltin oxide was reacted with the 2'-O-methylribonucleoside analogue followed by reaction with MeNPoc. Both 5'-O-MeNPoc and 3'-O-MeNPoc 2'-O-methylribonucleoside analogues were obtained.

Example 5

Hybridization to mixed-sequence oligodeoxynucleotide probes substituted with 2-amino-2'-deoxyadenosine (D)

To test the effect of a 2-amino-2'-deoxyadenosine (D) substitution in a heterogeneous probe sequence, two 4×4 oligodeoxynucleotide arrays were constructed using VLSIPS™ methodology and 5'-O-MeNPOC-protected deoxynucleoside phosphoramidites. Each array was comprised of the following set of probes based on the sequence (3')-CATCGTAGAA-(5') (SEQ ID NO:1):

1.-(HEG)-(3')-CATN$_1$GTAGAA-(5') (SEQ ID NO:14)
2.-(HEG)-(3')-CATCN$_2$TAGAA-(5') (SEQ ID NO:15)
3.-(HEG)-(3')-CATCGN$_3$AGAA-(5') (SEQ ID NO:16)
4.-(HEG)-(3')-CATCGTN$_4$GAA-(5') (SEQ ID NO:17)

where HEG=hexaethyleneglycol linker, and N is either A,G,C or T, so that probes are obtained which contain single mismatches introduced at each of four central locations in the sequence. The first probe array was constructed with all natural bases. In the second array, 2-amino-2'-deoxyadenosine (D) was used in place of adenosine (A). Both arrays were hybridized with a 5'-fluorescein-labeled oligodeoxynucleotide target, (5')-Fl-d(CTGAACGGTAGCATCTTGAC)-(3') (SEQ ID NO:18), which contained a sequence (in bold) complementary to the base probe sequence. The hybridization conditions were: 10 nM target in 5× SSPE buffer at 22° C. with agitation. After 30 minutes, the chip was mounted on the flowcell of a scanning laser confocal fluorescence microscope, rinsed briefly with 5× SSPE buffer at 22° C., and then a surface fluorescence image was obtained.

Figure 3:
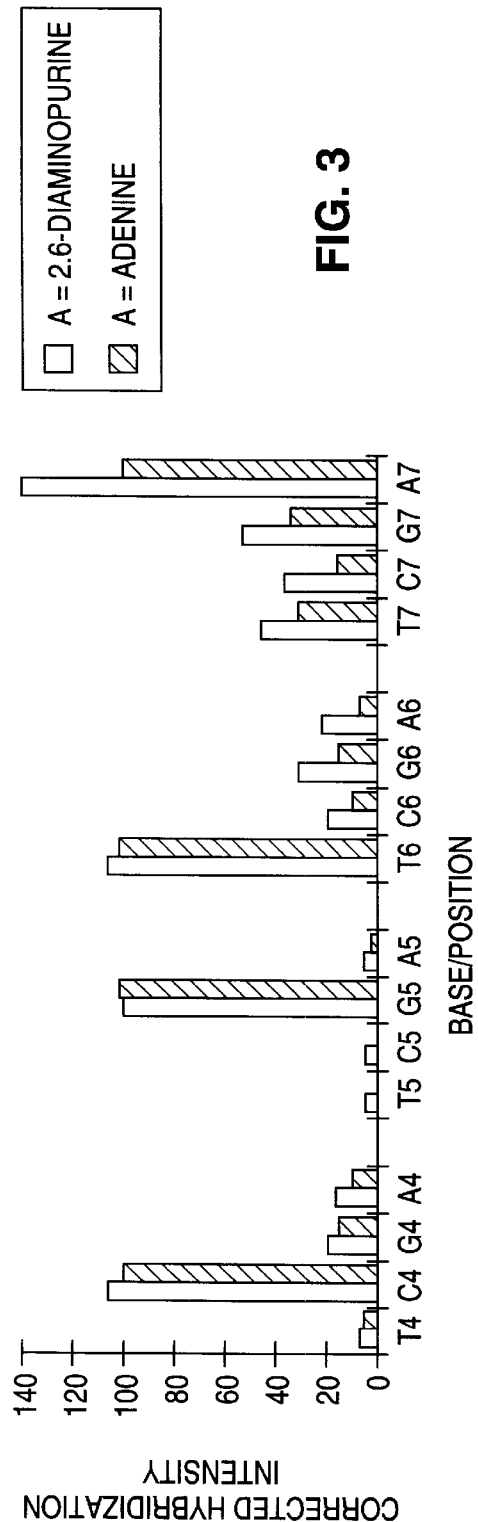
FIG. 3 shows the relative efficiency and specificity of hybridization for immobilized probe arrays containing adenine versus probe arrays containing 2,6-diaminopurine nucleotides. (3'-CATCGTAGAA-5' (SEQ ID NO:1)).

The relative efficiency of hybridization of the target to the complementary and single-base mismatched probes was determined by comparing the average bound surface fluorescence intensity in those regions of the of the array containing the individual probe sequences. The results (FIG. 3) show that a 2-amino-2'-deoxyadenosine (D) substitution in a heterogeneous probe sequence is a relatively neutral one, with little effect on either the signal intensity or the specificity of DNA-DNA hybridization, under conditions where the target is in excess and the probes are saturated.

Example 6

Hybridization to a dA-homopolymer oligodeoxynucleotide probe substituted with 2-amino-2'-deoxyadenosine (D)

The following experiment was performed to compare the hybridization of 2'-deoxyadenosine containing homopolymer arrays with 2-amino-2'-deoxyadenosine homopolymer arrays. The experiment was performed on two 11-mer oligodeoxynucleotide probe containing arrays. Two 11-mer oligodeoxynucleotide probe sequences were synthesized on a chip using 5'-O-MeNPOC-protected nucleoside phosphoramidites and standard VLSIPS™ methodology.

The sequence of the first probe was: (HEG)-(3')-d(AAAAANAAAAA)-(5') (SEQ ID NO:19); where HEG=hexaethyleneglycol linker, and N is either A,G,C or T. The second probe was the same, except that dA was replaced by 2-amino-2'-deoxyadenosine (D). The chip was hybridized with a 5'-fluorescein-labeled oligodeoxynucleotide target, (5')-Fl-d(TTTTTGTTTTT)-(3') (SEQ ID NO:20), which contained a sequence complementary to the probe sequences where N=C. Hybridization conditions were 10 nM target in 5× SSPE buffer at 22° C. with agitation. After 15 minutes, the chip was mounted on the flowcell of a scanning laser confocal fluorescence microscope, rinsed briefly with 5× SSPE buffer at 22° C. (low stringency), and a surface fluorescence image was obtained. Hybridization to the chip was continued for another 5 hours, and a surface fluorescence image was acquired again. Finally, the chip was washed briefly with 0.5× SSPE (high-stringency), then with 5× SSPE, and re-scanned.

Figure 4:
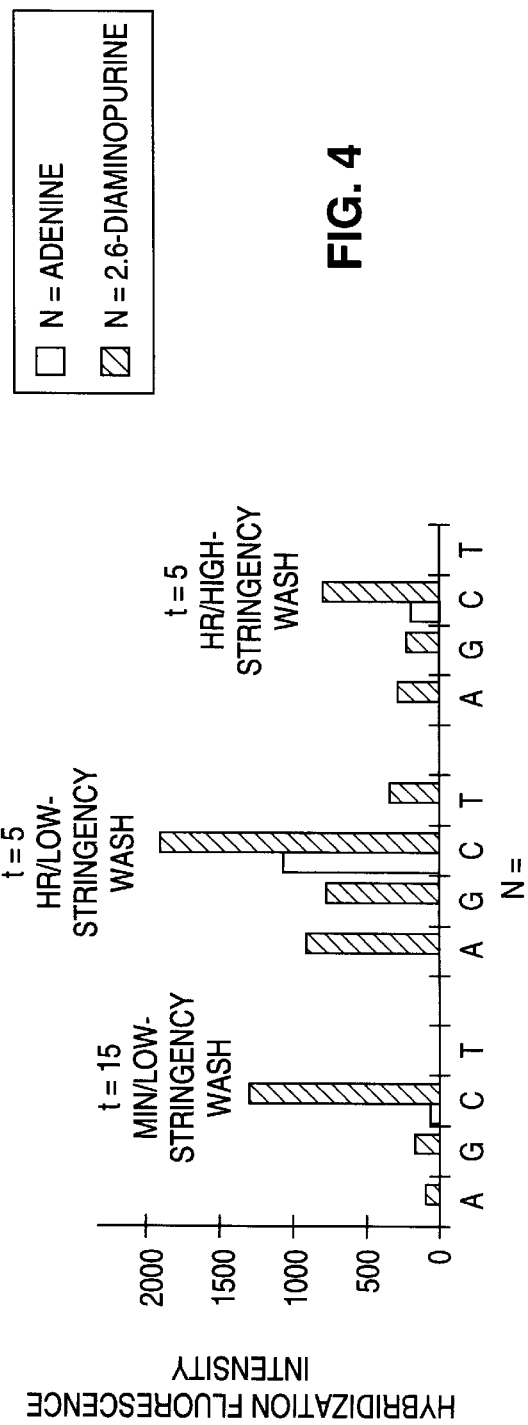
FIG. 4 shows the effect of substituting adenine with 2,6-diaminopurine (D) in immobilized poly-dA probe arrays. (AAAAANAAAAA (SEQ ID NO:2)).

The relative efficiency of hybridization of the target to the complementary and single-base mismatched probes was determined by comparing the average bound surface fluorescence intensity in those regions of the of the array containing the individual probe sequences. The results (FIG. 4) indicate that substituting 2'-deoxyadenosine with 2-amino-2'-deoxyadenosine in a d(A)$_n$ homopolymer probe sequence results in a significant enhancement in specific hybridization to a complementary oligodeoxynucleotide sequence.

Example 7

Hybridization to alternating A-T oligodeoxynucleotide probes substituted with 5-propynyl-2'-deoxyuridine (P) and 2-amino-2'-deoxyadenosine (D)

Commercially available 5'-DMT-protected 2'-deoxynucleoside/nucleoside-analog phosphoramidites (Glen Research) were used to synthesize two decanucleotide probe sequences on separate areas on a chip using a modified VLSIPS™ procedure. In this procedure, a glass substrate is initially modified with a terminal-MeNPOC-protected hexaethyleneglycol linker. The substrate was exposed to light through a mask to remove the protecting group from the linker in a checkerboard pattern. The first probe sequence was then synthesized in the exposed region using DMT-phosphoramidites with acid-deprotection cycles, and the sequence was finally capped with (MeO)$_2$PNiPr$_2$/tetrazole followed by oxidation. A second checkerboard exposure in a different (previously unexposed) region of the chip was then performed, and the second probe sequence was synthesized by the same procedure. The sequence of the first "control" probe was: -(HEG)-(3')-CGCGCCGCGC-(5') (SEQ ID NO:21); and the sequence of the second probe was one of the following:

1. -(HEG)-(3')-d(ATATAATATA)-(5') (SEQ ID NO:22)
2. -(HEG)-(3')-d(APAPAAPAPA)-(5') (SEQ ID NO:23)
3. -(HEG)-(3')-d(DTDTDDTDTD)-(5') (SEQ ID NO:24)
4. -(HEG)-(3')-d(DPDPDDPDPD)-(5') (SEQ ID NO:25)

where HEG=hexaethyleneglycol linker, A=2'-deoxyadenosine, T=thymidine, D=2-amino-2'-deoxyadenosine, and P=5-propynyl-2'-deoxyuridine. Each chip was then hybridized in a solution of a fluorescein-labeled oligodeoxynucleotide target, (5')-Fluorescein-d(TATATTATAT)-(HEG)-d(GCGCGGCGCG)-(3') (SEQ ID NO:26 and SEQ ID NO:27), which is complementary to both the A/T and G/C probes. The hybridization conditions were: 10 nM target in 5x SSPE buffer at 22° C. with gentle shaking. After 3 hours, the chip was mounted on the flowcell of a scanning laser confocal fluorescence microscope, rinsed briefly with 5x SSPE buffer at 22° C., and then a surface fluorescence image was obtained. Hybridization to the chip was continued overnight (total hybridization time=20hr), and a surface fluorescence image was acquired again.

Figure 5:
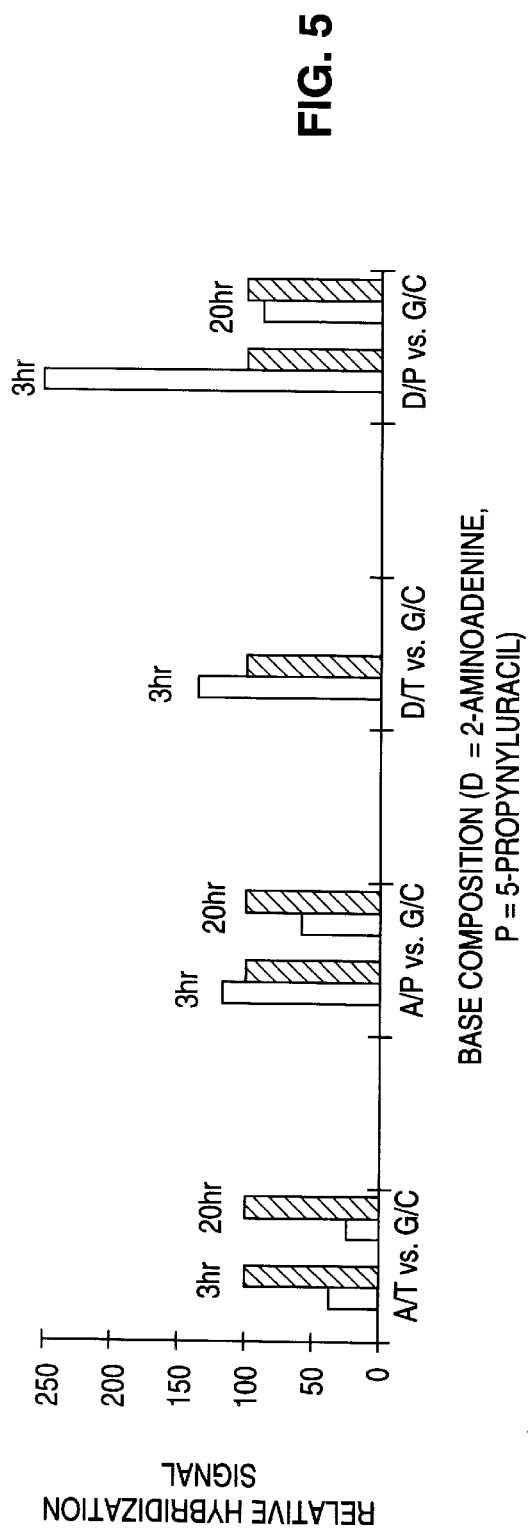
FIG. 5 shows the effects of substituting 5-propynyl-2'-deoxyuridine and 2-amino-2' deoxyadenosine in AT arrays on hybridization to a target nucleic acid. (ATATAATATA (SEQ ID NO:3) and CGCGCCGCGC (SEQ ID NO:4)).

The relative efficiency of hybridization of the target to the A/T and substituted A/T probes was determined by comparing the average surface fluorescence intensity bound to those parts of the chip containing the A/T or substituted probe to the fluorescence intensity bound to the G/C control probe sequence. The results (FIG. 5) show that 5-propynyl-dU and 2-amino-dA substitution in an A/T-rich probe significantly enhances the affinity of an oligonucleotide analogue for complementary target sequences. The unsubstituted A/T-probe bound only 20% as much target as the all-G/C-probe of the same length, while the D- & P-substituted A/T probe bound nearly as much (90%) as the G/C-probe. Moreover, the kinetics of hybridization are such that, at early times, the amount of target bound to the substituted A/T probes exceeds that which is bound to the all-G/C probe.

Example 8

Hybridization to oligodeoxynucleotide probes substituted with 7-deaza-2'-deoxyguanosine (ddG) and 2'-deoxyinosine (dI)

A 16x64 oligonucleotide array was constructed using VLSIPS™ methodology, with 5'-O-MeNPOC-protected nucleoside phosphoramidites, including the analogs ddG, and dI. The array was comprised of the set of probes represented by the following sequence: -(linker)-(3')-d(A T G T T G$_1$ G$_2$ G$_3$ G$_4$ G$_5$ C G G G T)-(5'); (SEQ ID NO:28) where underlined bases are fixed, and the five internal deoxyguanosines (G$_{1-5}$) are substituted with G, ddG, dI, and T in all possible (1024 total) combinations. A complementary oligonucleotide target, labeled with fluorescein at the 5'-end: (5')-Fl-d(C A A T A C A A C C C C C G C C C A T C C)-(3') (SEQ ID NO:29), was hybridized to the array. The hybridization conditions were: 5 nM target in 6x SSPE buffer at 22° C. with shaking. After 30 minutes, the chip was mounted on the flowcell of an Affymetrix scanning laser confocal fluorescence microscope, rinsed once with 0.25 x SSPE buffer at 22° C., and then a surface fluorescence image was acquired.

Figure 6:
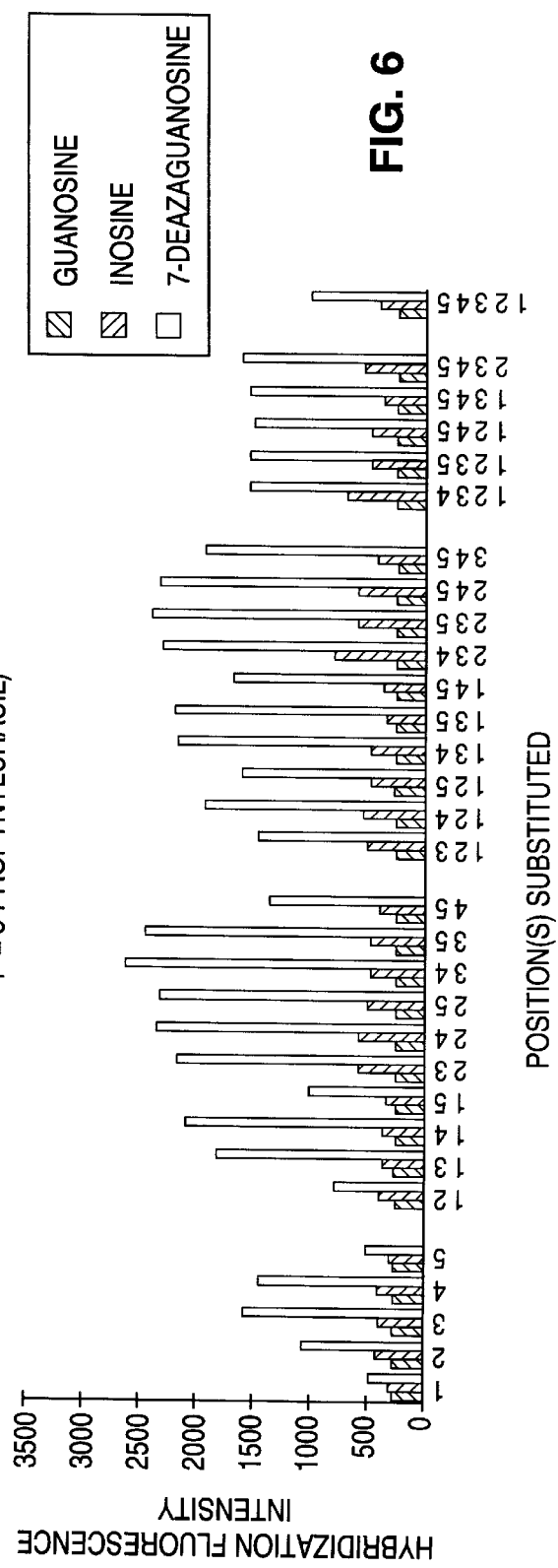
FIG. 6 shows the effects of dI and 7-deaza-dG substitutions in oligonucleotide arrays. (3'-ATGTT(G1G2G3G4G5) CGGGT-5' (SEQ ID NO:5)).

The "efficiency" of target hybridization to each probe in the array is proportional to the bound surface fluorescence intensity in the region of the chip where the probe was synthesized. The relative values for a subset of probes (those containing dG→ddG and dG→dI substitutions only) are shown in FIG. 6. Substitution of guanosine with 7-deazaguanosine within the internal run of five G's results in a significant enhancement in the fluorescence signal intensity which measures hybridization. Deoxyinosine substitutions also enhance hybridization to the probe, but to a lesser extent. In this example, the best overall enhancement is realized when the dG "run" is ~40–60% substituted with 7-deaza-dG, with the substitutions distributed evenly throughout the run (i.e., alternating dG/deaza-dG).

Example 9

Synthesis of 5'-MeNPOC-2'-deoxyinosine-3'-(N,N-diisopropyl-2-cyanoethyl)phosphoramidite 2'-deoxyinosine (5.0 g, 20 mmole) was dissolved in 50 ml of dry DMF, and 100 ml dry pyridine was added and evaporated three times to dry the solution. Another 50ml pyridine was added, the solution was cooled to −20° C. under argon, and 13.8 g (50 mmole) of MeNPOC-chloride in 20 ml dry DCM was then added dropwise with stirring over 60 minutes. After 60 minutes, the cold bath was removed, and the solution was allowed to stir overnight at room temperature. Pyridine and DCM were removed by evaporation, 500 ml of ethyl acetate was added, and the solution was washed twice with water and then with brine (200 ml each). The aqueous washes were combined and back-extracted twice with ethyl acetate, and then all of the organic layers were combined, dried with Na$_2$SO$_4$, and evaporated under vacuum. The product was recrystallized from DCM to obtain 5.0 g (50% yield) of pure 5'-O-MeNPOC-2'-deoxyinosine as a yellow solid (99% purity, according to $^1$H-NMR and HPLC analysis).

The MeNPOC-nucleoside (2.5 g, 5.1 mmole) was suspended in 60 ml of dry CH$_3$CN and phosphitylated with 2-cyanoethyl-N,N,N',N'-tetraisopropylphosphorodiamidite (1.65 g/1.66 ml; 5.5 mmole) and 0.47 g (2.7 mmole) of diisopropylammonium tetrazolide, according to the published procedure of Barone, et al. (*Nucleic Acids Res.* (1984) 12, 4051–61). The crude phosphoramidite was purified by flash chromatography on silica gel (90:8:2 DCM-MeOH-Et$_3$N), co-evaporated twice with anhydrous acetonitrile and dried under vacuum for ~24 hours to obtain 2.8 g (80%) of the pure product as a yellow solid (98% purity as determined by $^1$H/$^{31}$P-NMR and HPLC).

Example 10

Synthesis of 5'-MeNPOC-7-deaza-2'-deoxy(N2-isobutyryl)-guanosine-3'-(N,N-diisopropyl-2-cyanoethyl)phosphoramidite.

The protected nucleoside 7-deaza-2'-deoxy(N2-isobutyryl)guanosine (1.0 g, 3 mmole; Chemgenes Corp., Waltham, Mass.) was dried by co-evaporating three times with 5 ml anhydrous pyridine and dissolved in 5 ml of dry pyridine-DCM (75:25 by vol.). The solution was cooled to −45° C. (dry ice/CH$_3$CN) under argon, and a solution of 0.9 g (3.3 mmole) MeNPOC-Cl in 2 ml dry DCM was then added dropwise with stirring. After 30 minutes, the cold bath was removed, and the solution allowed to stir overnight at room temperature. The solvents were evaporated, and the crude material was purified by flash chromatography on silica gel (2.5%–5% MeOH in DCM) to yield 1.5 g (88% yield) 5'-MeNPOC-7-deaza-2'-deoxy(N2-isobutyryl) guanosine as a yellow foam. The product was 98% pure according to $^1$H-NMR and HPLC analysis.

The MeNPOC-nucleoside (1.25 g, 2.2 mmole) was phosphitylated according to the published procedure of Barone, et al. (*Nucleic Acids Res.* (1984) 12, 4051–61). The crude product was purified by flash chromatography on silica gel (60:35:5 hexane-ethyl acetate-Et$_3$N), co-evaporated twice with anhydrous acetonitrile and dried under vacuum for ~24 hours to obtain 1.3 g (75%) of the pure product as a yellow solid (98% purity as determined by $^1$H/$^{31}$P-NMR and HPLC).

Example 11

Synthesis of 5'-MeNPOC-2,6-bis(phenoxyacetyl) -2,6-diaminopurine-2'-deoxyriboside-3'-(N,N-diisopropyl-2-cyanoethyl)phosphoramidite.

The protected nucleoside 2,6-bis(phenoxyacetyl) -2,6-diaminopurine-2'-deoxyriboside (8 mmole, 4.2 g) was dried by coevaporating twice from anhydrous pyridine, dissolved in 2:1 pyridine/DCM (17.6 ml) and then cooled to −40° C. MeNPOC-chloride (8 mmole, 2.18 g) was dissolved in DCM (6.6 mls) and added to reaction mixture dropwise. The reaction was allowed to stir overnight with slow warming to room temperature. After the overnight stirring, another 2 mmole (0.6 g) in DCM (1.6 ml) was added to the reaction at −40° C. and stirred for an additional 6 hours or until no unreacted nucleoside was present. The reaction mixture was evaporated to dryness, and the residue was dissolved in ethyl acetate and washed with water twice, followed by a wash with saturated sodium chloride. The organic layer was dried with MgSO$_4$, and evaporated to a yellow solid which was purified by flash chromatography in DCM employing a methanol gradient to elute the desired product in 51% yield.

The 5'-MeNPOC-nucleoside (4.5 mmole, 3.5 g) was phosphitylated according to the published procedure of Barone, et al. (*Nucleic Acids Res.* (1984) 12, 4051–61). The crude product was purified by flash chromatography on silica gel (99:0.5:0.5 DCM-MeOH-Et$_3$N). The pooled fractions were evaporated to an oil, redissolved in a minimum amount of DCM, precipitated by the addition of 800 ml ice cold hexane, filtered, and then dried under vacuum for ~24 hours.

Overall yield was 56%, at greater than 96% purity by HPLC and $^1$H/$^{31}$P-NMR.

Example 12

5'-O-MeNPOC-protected phosphoramidites for incorporating 7-deaza-2'deoxyguanosine and 2'-deoxyinosine into VLSSIPS™ Oligonucleotide Arrays VLSIPS oligonucleotide probe arrays in which all or a subset of all guanosine residues are substitutes with 7-deaza-2'-deoxyguanosine and/or 2'-deoxyinosine are highly desirable. This is because guanine-rich regions of nucleic acids associate to form multi-stranded structures. For example, short tracts of G residues in RNA and DNA commonly associate to form tetrameric structures (Zimmermann et al. (1975) *J. Mol. Biol.* 92: 181; Kim, J. (1991) *Nature* 351: 331; Sen et al. (1988) *Nature* 335: 364; and Sunquist et al. (1989) *Nature* 342: 825). The problem this poses to chip hybridization-based assays is that such structures may compete or interfere with normal hybridization between complementary nucleic acid sequences. However, by substituting the 7-deaza-G analog into G-rich nucleic acid sequences, particularly at one or more positions within a run of G residues, the tendency for such probes to form higher-order structures is suppressed, while maintaining essentially the same affinity and sequence specificity in double-stranded structures. This has been exploited in order to reduce band compression in sequencing gels (Mizusawa, et al. (1986) N.A.R. 14: 1319) to improve target hybridization to G-rich probe sequences in VLSIPS arrays. Similar results are achieved using inosine (see also, Sanger et al. (1977) P.N.A.S. 74: 5463).

For facile incorporation of 7-deaza-2'-deoxyguanosine and 2'-deoxyinosine into oligonucleotide arrays using VLSIPS™ methods, a nucleoside phosphoramidite comprising the analogue base which has a 5'-O'-MeNPOC-protecting group is constructed. This building block was prepared from commercially available nucleosides according to Scheme I. These amidites pass the usual tests for coupling efficiency and photolysis rate.

SCHEME I

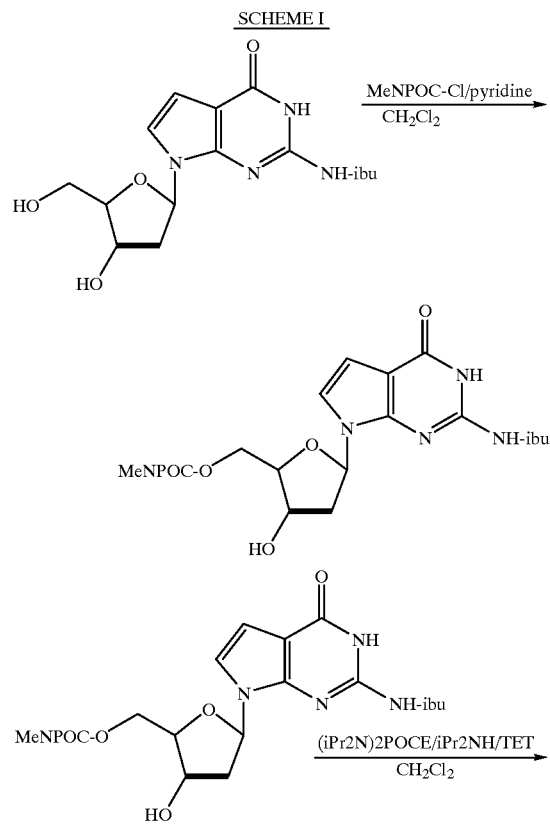

25
-continued

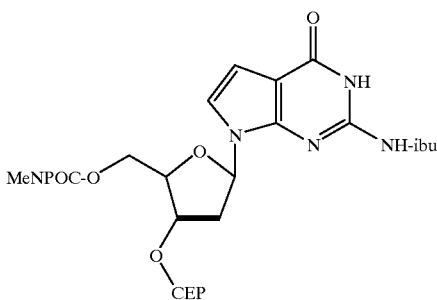

Although the foregoing invention has been described in some detail by way of illustration and example for purposes of clarity of understanding, modifications can be made thereto without departing from the spirit or scope of the appended claims.

All publications and patent applications cited in this application are herein incorporated by reference for all purposes as if each individual publication or patent application were specifically and individually indicated to be incorporated by reference.

What is claimed is:

1. A composition for analyzing interactions between oligonucleotide targets and oligonucleotide probes comprising an array of a plurality of oligonucleotide analogue probes having different sequences, wherein said oligonucleotide analogue probes are coupled to a solid substrate at known locations and wherein said plurality of oligonucleotide analogue probes are selected to bind to complementary oligonucleotide targets with a similar hybridization stability across the array.

2. The composition of claim 1, wherein at least one of said oligonucleotide analogue probes is selected to maintain hybridization specificity or mismatch discrimination with said complementary oligonucleotide targets.

3. The composition of claim 1, wherein at least one of said oligonucleotide analogue probes has increased the thermal stability between said oligonucleotide analogue probe and said complementary oligonucleotide target as compared to an oligonucleotide probe that is the perfect complement to the complementary oligonucleotide target with which said oligonucleotide analogue probe anneals.

4. The composition of claim 1, wherein at least one of said oligonucleotide analogue probes has decreased the thermal stability between said oligonucleotide analogue probe and said complementary oligonucleotide target as compared to an oligonucleotide probe that is the perfect complement to the complementary oligonucleotide target with which said oligonucleotide analogue probe anneals.

5. The composition of claim 2, wherein at least one of said oligonucleotide analogue probes has increased the thermal stability between said oligonucleotide analogue probe and said complementary oligonucleotide target as compared to an oligonucleotide probe that is the perfect complement to the complementary oligonucleotide target with which said oligonucleotide analogue probe anneals.

6. The composition of claim 2, wherein at least one of said oligonucleotide analogue probes has decreased the thermal stability between said oligonucleotide analogue probe and said complementary oligonucleotide target as compared to an oligonucleotide probe that is the perfect complement to the complementary oligonucleotide target with which said oligonucleotide analogue probe anneals.

7. The composition of claims 1–5 or 6, wherein said solid substrate is selected from the group consisting of silica, polymeric materials, glass, beads, chips, and slides.

8. The composition of claims 1–5 or 6, wherein said composition comprises an array of oligonucleotide analogue probes 5 to 20 nucleotides in length.

9. The composition of claims 1–5 or 6, wherein said array of oligonucleotide analogue probes comprises a nucleoside analogue with the formula

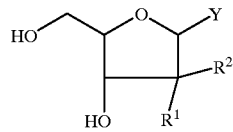

wherein:

the nucleoside analogue is not a naturally occurring DNA or RNA nucleoside;

$R^1$ is selected from the group consisting of hydrogen, methyl, hydroxyl, alkoxy, alkythio, halogen, cyano, and azido;

$R^2$ is selected from the group consisting of hydrogen, methyl, hydroxyl, alkoxy, alkythio, halogen, cyano, and azido;

Y is a heterocyclic moiety;

and wherein said nucleoside analogue is incorporated into the oligonucleotide analogue by attachment to a 3' hydroxyl of the nucleoside analogue, to a 5' hydroxyl of the nucleoside analogue, or both the 3' nucleoside and the 5' hydroxyl of the nucleoside analogue.

10. The composition of claims 1–5 or 6, wherein said array of oligonucleotide analogue probes comprises a nucleoside analogue with the formula

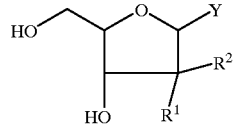

wherein:

the nucleoside analogue is not a naturally occurring DNA or RNA nucleoside;

$R^1$ is selected from the group consisting of hydrogen, hydroxyl, methyl, methoxy, ethoxy, propoxy, allyloxy, propargyloxy, Fluorine, Chlorine, and Bromine;

$R^2$ is selected from the group consisting of hydrogen, hydroxyl, methyl, methoxy, ethoxy, propoxy, allyloxy, propargyloxy, Fluorine, Chlorine, and Bromine; and Y is a base selected from the group consisting of purines, purine analogues pyrimidines, pyrimidine analogues, 3-nitropyrrole and 5-nitroindole;

and wherein said nucleoside analogue is incorporated into the oligonucleotide analogue by attachment to a 3' hydroxyl of the nucleoside analogue, to a 5' hydroxyl of the nucleoside analogue, or both the 3' nucleoside and the 5' hydroxyl of the nucleoside analogue.

11. The composition of claims 1–5 or 6, wherein each probe of said plurality of oligonucleotide analogue probes has at least one oligonucleotide analogue, and wherein at least one of said oligonucleotide analogues comprises a peptide nucleic acid.

12. The composition of claims 1–5 or 6, wherein at least one of said plurality of oligonucleotide analogue probes said array of oligonucleotide analogue probes is resistant to RNAase A.

13. The composition of claims 1–5 or 6, wherein said solid substrate is attached to over 1000 different oligonucleotide analogue probes.

14. The composition of claims 1–5 or 6, wherein each probe of said plurality of oligonucleotide analogue probes has at least one oligonucleotide analogue, and wherein at least one of said oligonucleotide analogues comprises 2'-O-methyl nucleotides.

15. The composition of claims 1–5 or 6, wherein said array of oligonucleotide analogue probes and said solid substrate comprises a plurality of different oligonucleotide analogue probes, each oligonucleotide analogue probes having the formula:

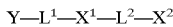

wherein,
Y is a solid substrate;
$X^1$ and $X^2$ are complementary oligonucteotides containing at least one nucleotide analogue;
$L^1$ is a spacer;
$L^2$ is a linking group having sufficient length such that $X^1$ and $X^2$ form a double-stranded oligonucleotide.

16. The composition of claim 15, wherein said composition comprises a library of unimolecular double-stranded oligonucleotide analogue probes.

17. The composition of claims 1–5 or 6, wherein said array of oligonucleotide analogue probes comprises a conformationally restricted array of oligonucleotide analogue probes with the formula:

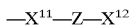

wherein $X^{11}$ and $X^{12}$ are complementary oligonucleotides or oligonucleotide analogues and Z is a presented moiety.

18. The composition of claims 1–5 or 6, wherein each probe of said plurality of oligonucleotide analogue probes has at least one oligonucleotide analogue, and wherein at least one of said oligonucleotide analogues comprises a nucleotide with a base selected from the group of bases consisting of 5-propynyluracil, 5-propynylcytosine, 2-aminoadenine, 7-deazaguanine, 2-aminopurine, 8-aza-7-deazaguanine, 1H-purine, and hypoxanthine.

19. The composition of claims 1–5 or 6, wherein said plurality of oligonucleotide analogue probes are coupled to said solid substrate by light-directed chemical coupling.

20. The composition of claim 19, wherein said solid substrate is derivitized with a silane reagent prior to synthesis of said plurality of oligonucleotide analogue probes.

21. The composition of claims 1–5 or 6, wherein said plurality of oligonucleotide analogue probes are coupled to said solid substrate by flowing oligonucleotide analogue reagents over known locations of the solid substrate.

22. The composition of claim 21, wherein said solid substrate is derivitized with a silane reagent prior to synthesis of said plurality of oligonucleotide analogue probes.

23. The composition of claims 1–5 or 6, wherein at least one of plurality of said oligonucleotide analogue probes forms a first duplex with a target oligonucleotide sequence, wherein said oligonucleotide analogue probe has a corresponding oligonucleotide sequence that forms a second duplex with said target oligonucleotide sequence, wherein said second duplex is rich in A-T or G-C nucleotide pairs, and wherein said oligonucleotide analogue probe has at least one nucleotide analogue in place of an A, T, G, or C nucleotide of said corresponding oligonucleotide sequence at a position within said oligonucleotide analogue probe such that said first duplex has an increased hybridization stability than said second duplex.

24. The composition of claim 23, wherein said oligonucleotide analogue probe contains fewer bases than said corresponding oligonucleotide sequence.

25. The composition of claims 1–5 or 6, wherein said oligonucleotide analogue probe forms a first duplex with a target oligonucleotide sequence, wherein said oligonucleotide analogue probe has a corresponding oligonucleotide sequence that forms a second duplex with said target polynucleotide sequence, and wherein said oligonucleotide analogue probe is shorter than said corresponding polynucleotide sequence.

26. A composition for analyzing the interaction between an oligonucleotide target and an oligonucleotide probe comprising an array of a plurality of oligonucleotide probes having different sequences hybridized to complementary oligonucleotide analogue targets, wherein said oligonucleotide analogue targets bind to complementary oligonucleotide probes with a similar hybridization stability across the array.

27. The composition of claim 26, wherein at least one of said oligonucleotide analogue target is selected to maintain hybridization specificity or mismatch discrimination with said complementary oligonucleotide probes.

28. The composition of claim 26, wherein at least one of said oligonucleotide analogue targets has increased the thermal stability between said oligonucleotide analogue target and said complementary oligonucleotide probe as compared to an oligonucleotide target that is the perfect complement to the complementary oligonucleotide probe with which said oligonucleotide analogue target anneals.

29. The composition of claim 26, wherein at least one of said oligonucleotide analogue targets has decreased the thermal stability between said oligonucleotide analogue target and said complementary oligonucleotide probe as compared to an oligonucleotide target that is the perfect complement to the complementary oligonucleotide probe with which said oligonucleotide analogue target anneals.

30. The composition of claim 27, wherein at least one of said oligonucleotide analogue targets has increased the thermal stability between said oligonucleotide analogue target and said complementary oligonucleotide probe as compared to an oligonucleotide target that is the perfect complement to the complementary oligonucleotide probe with which said oligonucleotide analogue target anneals.

31. The composition of claim 27, wherein at least one of said oligonucleotide analogue targets has decreased the thermal stability between said oligonucleotide analogue target and said complementary oligonucleotide probe as compared to an oligonucleotide target that is the perfect complement to the complementary oligonucleotide probe with which said oligonucleotide analogue target anneals.

32. The composition of claims 26–30 or 31, wherein the oligonucleotide analogue target is a PCR amplicon.

33. The composition of claims 26–30 or 31, wherein at least one of said plurality of oligonucleotide probes comprise at least one oligonucleotide analogue.

34. The composition of claims 26–30 or 31, wherein at least one target oligonucleotide analogue acid is an RNA nucleic acid.

35. A method analyzing interactions between an oligonucleotide target and an oligonucleotide probe, comprising the steps of:
  (a). synthesizing an oligonucleotide analogue array comprising a plurality of oligonucleotide analogue probes having different sequences, wherein said oligonucleotide analogue probes are coupled to a solid substrate at known locations, said solid substrate having a surface;
  (b). exposing said oligonucleotide analogue probe array to a plurality of oligonucleotide targets under hybridization conditions such that said plurality of oligonucleotide analogue probes bind to complementary oligonucleotide targets with a similar hybridization stability across the array; and
  (c). determining whether an oligonucleotide analogue probe of said oligonucleotide analogue probe array binds to at least one of said target nucleic acids.

36. The method in accordance of claim 35, wherein at least one of said oligonucleotide analogue probes is selected to maintain hybridization specificity or mismatch discrimination with said complementary oligonucleotide targets.

37. The method in accordance of claim 35, wherein at least one of said oligonucleotide analogue probes has increased the thermal stability between said oligonucleotide analogue probe and said complementary oligonucleotide target as compared to an oligonucleotide probe that is the perfect complement to the complementary oligonucleotide target with which said oligonucleotide analogue probe anneals.

38. The method in accordance of claim 35, wherein at least one of said oligonucleotide analogue probes has decreased the thermal stability between said oligonucleotide analogue probe and said complementary oligonucleotide target as compared to an oligonucleotide probe that is the perfect complement to the complementary oligonucleotide target with which said oligonucleotide analogue probe anneals.

39. The method in accordance of claim 36, wherein at least one of said oligonucleotide analogue probes has increased the thermal stability between said oligonucleotide analogue probe and said complementary oligonucleotide target as compared to an oligonucleotide probe that is the perfect complement to the complementary oligonucleotide target with which said oligonucleotide analogue probe anneals.

40. The method in accordance of claim 36, wherein at least one of said oligonucleotide analogue probes has decreased the thermal stability between said oligonucleotide analogue probe and said complementary oligonucleotide target as compared to an oligonucleotide probe that is the perfect complement to the complementary oligonucleotide target with which said oligonucleotide analogue probe anneals.

41. The method of claims 35–39 or 40, wherein said oligonucleotide target is selected from the group comprising genomic DNA, cDNA, unspliced RNA, mRNA, and rRNA.

42. The method of claims 35–39 or 40, wherein said target nucleic acid is amplified prior to said hybridization step.

43. The method of claims 35–39 or 40, wherein said plurality of oligonucleotide analogue probes is synthesized on said solid support by light-directed synthesis.

44. The method of claims 35–39 or 40, wherein said plurality of said oligonucleotide analogue probes is synthesized on said solid support by causing oligonucleotide analogue synthetic reagents to flow over known locations of said solid support.

45. The method of claims 35–39 or 40, wherein said step (a). comprises the steps of:
  i). forming a plurality of channels adjacent to the surface of said substrate;
  ii). placing selected reagents in said channels to synthesize oligonucleotide analogue probes at known locations; and
  iii). repeating steps i). and ii). thereby forming an array of oligonucleotide analogue probes having different sequences at known locations on said substrate.

46. The method of claims 35–39 or 40, wherein said solid substrate is selected from the group consisting of beads, slides, and chips.

47. The method of claims 35–39 or 40, wherein said solid substrate is comprised of materials selected from the group consisting of silica, polymers and glass.

48. The method of claims 35–39 or 40, wherein the oligonucleotide analogue probes of said array are synthesized using photoremovable protecting groups.

49. The method of claims 35–39 or 40, further comprising selectively incorporating MeNPoc onto the 3' or 5' hydroxyl of at least one nucleoside analogue and selectively incorporating said nucleoside analogue into at least one of said oligonucleotide analogue probes.

50. The method of claims 35–39 or 40, wherein at least one of said oligonucleotide analogue probes is synthesized from phosphoramidite nucleoside reagents.

51. A method of detecting an oligonucleotide target, comprising enzymatically copying an oligonucleotide target using at least one nucleotide analogue, thereby producing multiple oligonucleotide analogue targets, selecting said oligonucleotide analogue targets such that said oligonucleotide analogue targets bind to the complementary oligonucleotide probes coupled to a solid surface at known locations of an array with a similar hybridization stability across the array, hybridizing the oligonucleotide analogue targets to complementary oligonucleotide probes, and detecting whether at least one of said oligonuclotide analogue targets binds to said complementary oligonucleotide acid probe.

52. The method of claim 51, wherein at least one of said oligonucleotide analogue targets is selected to maintain hybridization specificity or mismatch discrimination with said complementary oligonucleotide probes.

53. The method of claim 51, wherein at least one of said oligonucleotide analogue targets has increased the thermal stability between said oligonucleotide analogue target and said complementary oligonucleotide probe as compared to an oligonucleotide target that is the perfect complement to the complementary oligonucleotide probe with which said oligonucleotide analogue target anneals.

54. The method of claim 51, wherein at least one of said oligonucleotide analogue targets has decreased the thermal stability between said oligonucleotide analogue target and said complementary oligonucleotide probe as compared to an oligonucleotide target that is the perfect complement to the complementary oligonucleotide probe with which said oligonucleotide analogue target anneals.

55. The method of claim 52, wherein at least one of said oligonucleotide analogue targets has increased the thermal stability between said oligonucleotide analogue target and said complementary oligonucleotide probe as compared to an oligonucleotide target that is the perfect complement to the complementary oligonucleotide probe with which said oligonucleotide analogue target anneals.

56. The method of claim 52, wherein at least one of said oligonucleotide analogue targets has decreased the thermal stability between said oligonucleotide analogue target and said complementary oligonucleotide probe as compared to an oligonucleotide target that is the perfect complement to the complementary oligonucleotide probe with which said oligonucleotide analogue target anneals.

57. The method of claims 51–55 or 56, wherein the oligonucleotide probe array comprises at least one oligonucleotide analogue probe which is complementary to at least one of said oligonucleotide analogue targets.

58. A method of making an array of oligonucleotide probes, comprising providing a plurality of oligonucleotide analogue probes having at least one oligonucleotide analogue, said oligonucleotide analogue probes having different sequences at known locations on an array, selecting the oligonucleotide analogue probes to hybridize with complementary oligonucleotide target sequences under hybridization conditions such that said oligonucleotide analogue probes bind to complementary oligonucleotide targets with a similar hybridization stability, across the array.

59. The method of claim 58, wherein at least one of said oligonucleotide analogue probes is selected to maintain hybridization specificity or mismatch discrimination with said complementary oligonucleotide targets.

60. The method of claim 58, wherein at least one of said oligonucleotide analogue probes has increased the thermal stability between said oligonucleotide analogue probe and said complementary oligonucleotide target as compared to an oligonucleotide probe that is the perfect complement to the complementary oligonucleotide target with which said oligonucleotide analogue probe anneals.

61. The method of claim 58, wherein at least one of said oligonucleotide analogue probes has decreased the thermal stability between said oligonucleotide analogue probe and said complementary oligonucleotide target as compared to an oligonucleotide probe that is the perfect complement to the complementary oligonucleotide target with which said oligonucleotide analogue probe anneals.

62. The method of claim 59, wherein at least one of said oligonucleotide analogue probes has increased the thermal stability between said oligonucleotide analogue probe and said complementary oligonucleotide target as compared to an oligonucleotide probe that is the perfect complement to the complementary oligonucleotide target with which said oligonucleotide analogue probe anneals.

63. The method of claim 59, wherein at least one of said oligonucleotide analogue probes has decreased the thermal stability between said oligonucleotide analogue probe and said complementary oligonucleotide target as compared to an oligonucleotide probe that is the perfect complement to the complementary oligonucleotide target with which said oligonucleotide analogue probe anneals.

64. The method in accordance with claims 58–62, or 63, further comprising incorporating at least one oligonucleotide analogue into at least one of the oligonucleotide analogue probes of the array to reduce or prevent the formation of secondary structure in the oligonucleotide of the array.

65. The method in accordance with claims 58–62, or 63, further comprising incorporating at least one oligonucleotide analogue into at least one of the oligonucleotide target to reduce or prevent the formation of secondary structure in the target polynucleotide sequence.

66. The method in accordance with claims 58–62, or 63, further comprising incorporating at least one oligonucleotide analogue into at least one of the oligonucleotide analogue probes of the array to create secondary structure in the oligonucleotide of the array.

67. The method in accordance with claims 58–62, or 63, further comprising incorporating a base selected from the group consisting of 5-propynyluracil, 5-propynylcytosine, 2-aminoadenine, 7-deazaguanine, 2-aminopurine, 8-aza-7-deazaguanine, 1H-purine, and hypoxanthine into the oligonucleotide analogue probes of the array.

68. The method of claim 67 further comprising selecting said at least one oligonucleotide analogue such that the oligonucleotide analogue probe is a homopolymer.

69. The method in accordance with claims 58–62, or 63, further comprising selecting said at least one oligonucleotide analogue from the group consisting essentially of oligonucleotide analogues comprising 2'-O-methyl nucleotides and oligonucleotides comprising a base selected from the group of bases consisting of 5 -propynyluracil, 5-propynylcytosine, 7-deazaguanine, 2-aminoadenine, 8-aza-7-deazaguanine, 1H-purine, and hypoxanthine.

70. The method in accordance with claims 58–62 or 63, further comprising selecting said at least one oligonucleotide analogue such that oligonucleotide analogue probes comprises at least one peptide nucleic acid.

71. The method in accordance with claims 58–62, or 63, further comprising selecting said at least one oligonucleotide analogue to increase image brightness when the oligonucleotide target and the oligonucleotide analogue probe hybridize in the presence of a fluorescent indicator, in comparison to a oligonucleotide probe without oligonucleotide analogs.

72. The method in accordance with claims 58–62, or 63, further comprising providing said plurality of oligonucleotide analogue probes in an array with at least 1000 other oligonucleotide analogue probes.

* * * * *

Adverse Decisions in Interference

Patent No. 6,156,501, Glenn H. McGall, Charles G. Miyada, Maureen Cronin, Jennifer D. Tan and Mark S. Chee, ARRAYS OF MODIFIED NUCLEIC ACID PROBES AND METHODS OF USE, Interference No. 105,351, final judgment adverse to the patentees rendered January 4, 2010, as to claims 1-72.

(*Official Gazette*, *July 27, 2010*)

UNITED STATES PATENT AND TRADEMARK OFFICE
CERTIFICATE OF CORRECTION

| | |
|---|---|
| PATENT NO. | : 6,156,501 |
| APPLICATION NO. | : 08/630427 |
| DATED | : December 5, 2000 |
| INVENTOR(S) | : Glenn McGall et al. |

It is certified that error appears in the above-identified patent and that said Letters Patent is hereby corrected as shown below:

Column 1, line 15, following "Cross-Reference to Related Application" paragraph, please insert the following:

-- GOVERNMENT INTEREST

The present invention was made with U.S. Government support under ATP Grant No. 70NANB5H1031, and the Government may have certain rights in the invention. --

Signed and Sealed this

Seventh Day of September, 2010

David J. Kappos
*Director of the United States Patent and Trademark Office*